United States Patent
Tagawa et al.

(10) Patent No.: US 9,606,072 B2
(45) Date of Patent: Mar. 28, 2017

(54) RADIATION INSPECTING APPARATUS

(71) Applicant: SHIMADZU CORPORATION, Kyoto (JP)

(72) Inventors: Yusuke Tagawa, Kyoto (JP); Hiroshi Oohara, Kyoto (JP); Yoshihiro Ueno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/735,112

(22) Filed: Jun. 9, 2015

(65) Prior Publication Data
US 2016/0363544 A1    Dec. 15, 2016

(51) Int. Cl.
G01N 23/04    (2006.01)
G01T 7/08    (2006.01)

(52) U.S. Cl.
CPC .............. *G01N 23/046* (2013.01); *G01T 7/08* (2013.01)

(58) Field of Classification Search
USPC .......................................................... 378/22
See application file for complete search history.

(56) References Cited

U.S. PATENT DOCUMENTS

| | | | | |
|---|---|---|---|---|
| 5,270,631 A * | 12/1993 | Takahashi | ............ | G05B 19/232 318/135 |
| 5,681,260 A * | 10/1997 | Ueda | .................. | A61B 1/00082 128/899 |
| 6,459,759 B1 * | 10/2002 | Tominaga | ............ | G01N 23/046 378/22 |
| 6,590,355 B1 * | 7/2003 | Kikuchi | .............. | G03F 7/70716 310/12.06 |
| 9,476,844 B2 * | 10/2016 | Tagawa | ................ | G01N 23/046 |
| 2004/0096029 A1 | 5/2004 | Shiota et al. | | |
| 2004/0177520 A1 | 9/2004 | Nakamura et al. | | |
| 2004/0252811 A1 | 12/2004 | Morita et al. | | |
| 2014/0205058 A1 * | 7/2014 | Tagawa | ................ | G01N 23/046 378/11 |

FOREIGN PATENT DOCUMENTS

| | | |
|---|---|---|
| JP | 2004-156927 A | 6/2004 |
| JP | 2004-223647 A | 8/2004 |
| JP | 3694833 B2 | 9/2005 |
| JP | 2006-162335 A | 6/2006 |
| JP | 2008-292383 A | 12/2008 |
| JP | 2010-002221 A | 1/2010 |
| JP | 4415762 B2 | 2/2010 |

* cited by examiner

*Primary Examiner* — Phillip A Johnston
(74) *Attorney, Agent, or Firm* — McDermott Will & Emery LLP

(57) ABSTRACT

In an X-ray inspecting apparatus, a rotational fluctuation amount of a stage is calculated around a power transmission part of the stage and a stage drive unit as a base point, i.e., the X-axis and Y-axis sliding parts, in accordance with detected positional information from a position detecting sensor. Then, a stage shift amount is calculated in accordance with the rotational fluctuation amount and a distance between the base point and an imaging position on the stage. Here, the stage shift amount corresponds to a positional deviation of the stage at the imaging position caused by an attitude variation of the stage in a yawing direction, and thus is an error in repeated positioning. Accordingly, a tomographic image with high resolution can be generated in consideration of the error in repeated positioning.

13 Claims, 14 Drawing Sheets

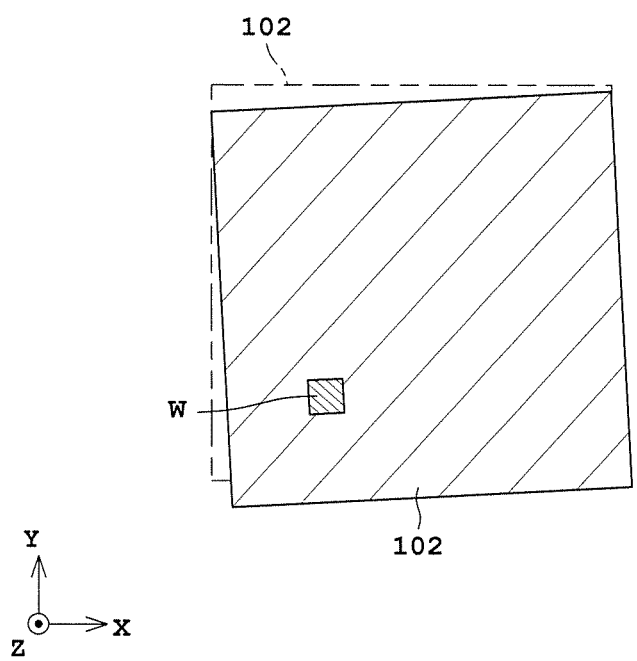

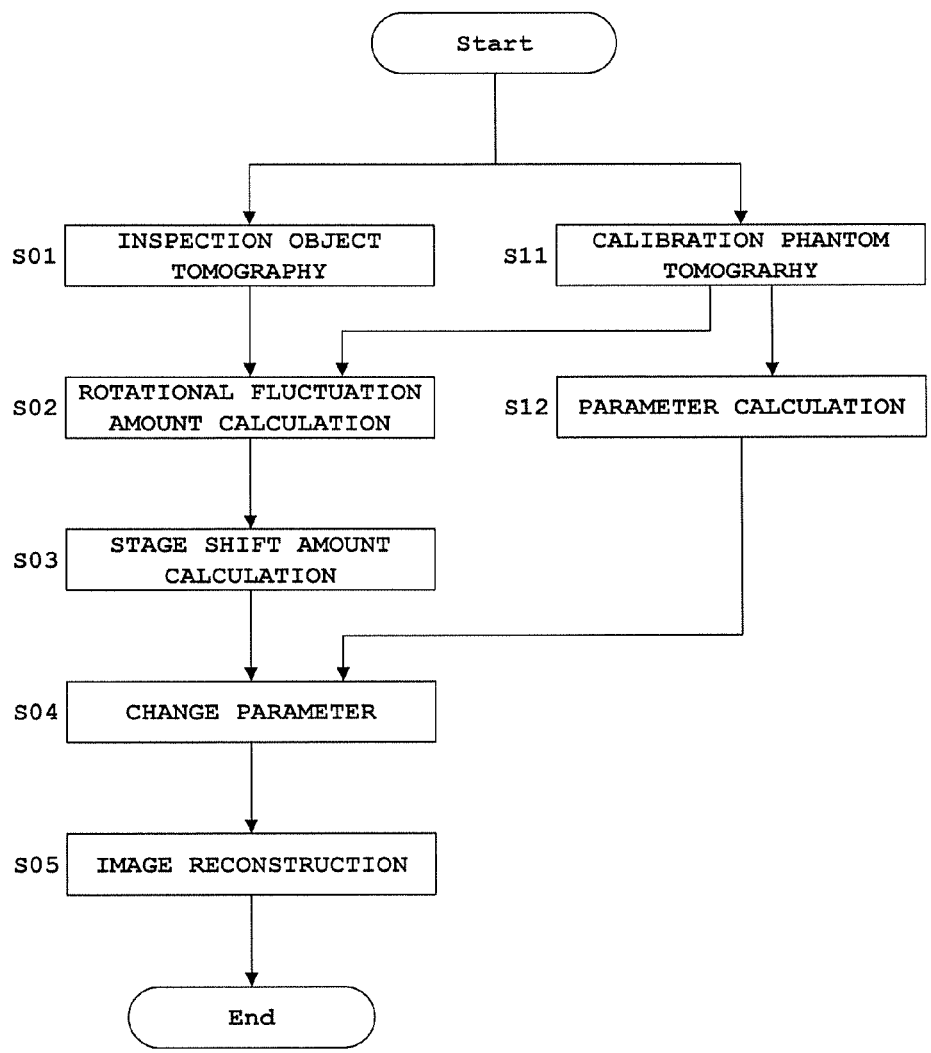

RADIATION INSPECTING APPARATUS

CROSS-REFERENCE TO RELATED APPLICATIONS

This application is the U.S. equivalent of Japanese Patent Application No. JP2012-270250 filed Dec. 11, 2012, which published as Japanese Patent Publication (Unexamined) No. JP2014-115216A, on Jun. 26, 2014. The subject matter of this Japanese Application is incorporated by reference in entirety.

TECHNICAL FIELD

The present invention relates to a radiation inspecting apparatus used for inspection of electronic components, such as BGA (Ball Grid Array), substrate wires, joining parts of a solder and voids, or inspection of interior defects of other inspection objects.

BACKGROUND ART

Examples of such currently-used apparatus include an X-ray CT apparatus. The X-ray CT apparatus includes a radiation source and a detector disposed horizontally so as to face to each other, and a stage between the radiation source and the detector. An inspection object is placed on the stage, and the stage is rotated around a rotation axis, whereby projection images are captured from various angles. Then, the captured projection images are reconstructed to obtain a three-dimensional image such as a tomographic image.

Such an X-ray CT apparatus sometimes requires an increased magnification rate upon inspection of an inspection object having an extremely minute configuration, such as BGA and wires, through tomography. To increase the magnification rate, the radiation source has to be moved close to the inspection object. However, the following drawback may arise when a radiation source 103 faces to a detector 104 horizontally, and an inspection object W is large in a plane direction, as illustrated by chain double-dashed lines in FIG. 1. That is, if the radiation source 103 is moved close to an inspection object W, interference may occur between the radiation source 103 and the inspection object W or between the radiation source 103 and a stage 102. Accordingly, the magnification rate cannot be increased so largely. Then, tomography (Planar Computed Tomography: PCT) has been known as illustrated by solid lines in FIG. 1. That is, the radiation source 103 and the detector 104 are disposed obliquely relative to a plane orthogonal to a rotation axis R for suppressing interference to the inspection object W.

Moreover, a method as illustrated in FIG. 2A other than that in FIG. 1 implements the PCT. See, for example, Japanese Unexamined Patent Publications No. 2010-002221A and 2006-162335A as well as Japanese Patent No. 3694833. Specifically, a radiation source 103 is fixedly disposed for emitting X-rays upward around the rotation axis R in a widespread manner. Tomography is conducted by translating a stage 102 supporting an inspection object W placed thereon around the rotation axis R in circular orbit and rotating a detector 104 around the rotation axis R in synchronization with the movement of the stage 102.

FIG. 2B illustrates a plan view of the stage 102 in FIG. 2A. Stage drive units 137 and 147 are each disposed adjacent to one edge of the stage 102 in FIG. 2B for driving the stage 102. Guiding units 135 and 145 such as guide rails are each disposed on both edges of the stage 102 facing to each other. The stage 102 has an imaging area surrounded with the stage drive units 137 and 147 and the guiding units 135 and 145. The imaging area is hollow with a certain space. See, for example, Japanese Unexamined Patent Publications No. 2008-292383A and 2004-223647A. Such a configuration is intended to prevent an object with low radiolucency from entering into the imaging area and preventing physical interference between the radiation source 103 and the stage drive units 137 and 147.

The apparatus illustrated in FIG. 2A includes drive systems each having the detector 104 and the stage 102 individually. As a result, obtaining an ideal scanning orbit for tomography requires high-accurate positioning as well as a mechanism and control for synchronization of the driving systems. Accordingly, the apparatus becomes expensive. Then, another method has been suggested as following. That is, even when some positional variation exists between actual and ideal scanning orbits, calibration is performed with a calibration phantom to calculate a geometrical positional deviation from the ideal scanning orbit and store the positional deviation as a parameter for correcting the positional deviation upon image reconstruction. See, for example, Japanese Patent No. 4415762.

On the other hand, inspection using projection images has been conventionally performed with a typical X-ray fluoroscopy apparatus. When such an apparatus inspects an inspection object with an extremely minute configuration such as BGA or wires, radiography through oblique emission of X-rays or a high magnification rate is sometimes required. In such a case, a tracking function has been suggested that performs tracking while an attention point of a sample is maintained at the center of the field of view in a fluoroscopy image even with a variation in inclination of X-rays or magnification rate. See, for example, Japanese Patent Publication No. 2004-156927A.

SUMMARY OF INVENTION

Technical Problem

Upon the inspection with the X-ray CT apparatus with the method suggested in the Japanese Patent No. 4415762 mentioned above to perform calibration in advance, errors in positioning of the drive system such as the stage drive units 137 and 147 can be eliminated. On the other hand, it is difficult to eliminate an error in repeated positioning of the stage 102. The error in repeated positioning is, for example, a minute positional deviation caused by a play (rattle) between a fixed portion and movable portions of the guiding units 135 and 145, each movably holding the stage 102. Such an error leads to low reproducibility of positioning the stage 102, and contain variations. Consequently, the error in repeated positioning appears as an error from a parameter for correcting the positional deviation. Such a drawback may arise. Especially, when the inspection object W is imaged with a high magnification rate by approaching the radiation source 103 to the stage 102, the error in repeated positioning of the stage 102 exerts a large influence on the tomographic image.

Specifically, the stage 102 of the radiation inspecting apparatus illustrated in FIG. 2B is hollow with the guiding units 135 and 145 as well as the stage drive units 137 and 147 being disposed adjacent to the edges of the stage 102. Accordingly, even with a drive system having excellent accuracy for repeated positioning on one edge adjacent to a driving axis, it is likely to occur that an inconstant attitude variation such as a variation in a yawing direction (denoted by the numeral B in FIG. 2B) around a base point of a power transmitter of the stage 102 and the stage drive units 137 and 147. Such a drawback may be possessed. Here, the attitude variation is a rotation variation from the stage drive units 137 and 147. Consequently, the attitude variation increases as a distance to the stage drive units 137 and 147 becomes long. That is, an imaging position IP2 in FIG. 2B is further from the stage drive units 137 and 147 than an imaging position IP1. Accordingly, the imaging position IP2 has a larger attitude variation of the stage 102 in the yawing direction B. This causes an attitude variation of the stage 102 as illustrated in FIG. 3. Such an attitude variation differs depending on stage's drive. As a result, it is impossible to confirm the attitude variation prior to taking a tomographic image. Japanese Patent No. 4415762 discloses the feature to obtain deviation from ideal movement of the stage prior to radiography. Consequently, the feature cannot correspond to the above attitude variation.

It is conceivable to adopt the configuration disclosed in Japanese Patent Publication No. 2004-223647 in order to solve the drawback about the attitude variation. That is, Japanese Patent Publication No. 2004-223647 discloses a stage having an enhanced restraint force in the yawing direction B (a resistance force against twist). On the other hand, the number of guiding units 135 and 145 and holders increases, and correspondingly the apparatus becomes expensive. In addition, a sufficient restraint force is not ensured. Such a drawback may arise. For another solution, a configuration is conceivable that stage drive units are disposed on both edges of the stage 102. Such causes a complex system of an apparatus and correspondingly the apparatus becomes expensive. Such another drawback may also arise.

Moreover, the error in repeated positioning mentioned above exerts an influence on the inspection with the fluoroscopy apparatus. For instance, a projection image is obtained on a position of the stage and then the position is moved to another position. Thereafter, the moved position is returned to its original position and a projection image is captured at the original position. In such a case, a projection image with a positional deviation may be displayed similarly. Such a drawback may arise. Alternatively, the following drawback may arise. That is, an attention point of an inspection object W is registered in an inspecting apparatus. When a magnification rate or projection angle is changed, the stage 102 deviates, and thus a tracking function that always tracks the attention point at the center of the projection image causes the attention point to deviate from the center of the projection image.

The present invention has been made regarding the state of the art noted above, and its one object is to provide a radiation inspecting apparatus that allows generation of a tomographic image with high resolution or a projection image with high-accurate positioning even when some inconstant attitude variation causes insufficient repeated positioning accuracy.

SOLUTION TO PROBLEM

The present invention is constituted as stated below to achieve the above object. One embodiment of the present invention discloses a radiation inspecting apparatus having a radiation source emitting radiation to an inspection object, a radiation detector detecting radiation passing through the inspection object to capture projection images, and a stage disposed between the radiation source and the radiation detector for supporting the inspection object placed thereon. The apparatus includes a stage drive unit moving the stage; a position detecting sensor detecting a position of the stage; a rotational fluctuation amount calculating unit calculating a rotational fluctuation amount of the stage around a power transmission part of the stage and the stage drive unit as a base point in accordance with detected positional information from the position detecting sensor upon imaging of the inspection object; a stage shift amount calculating unit calculating a stage shift amount in accordance with the rotational fluctuation amount and a distance between the base point and an imaging position on the stage, the stage shift amount representing a stage shift amount at the imaging position; and an image reconstructing unit correcting a positional deviation of the stage in accordance with the stage shift amount and reconstructing the projection images of the inspection object captured from various directions to generate a tomographic image.

With the radiation inspecting apparatus according to the embodiment of the present invention, the rotational fluctuation amount of the stage is calculated around the power transmission part of the stage and the stage drive unit as the base point in accordance with the detected positional information from the position detecting sensor upon capturing the inspection object. Then, the stage shift amount representing the fluctuation amount of the stage at the imaging position is calculated in accordance with the rotational fluctuation amount and the distance between the base point and the imaging position on the stage. That is, the stage shift amount at the imaging position is calculated from the rotational fluctuation amount of the stage around the base point and the distance between the base point and the imaging position on the stage. Here, the stage shift amount corresponds to a positional deviation of the stage at the imaging position caused by the attitude variation of the stage in a yawing direction, and thus is an error in repeated positioning. Accordingly, the positional deviation of the stage is corrected in accordance with the stage shift amount, and the projection images of the inspection object captured in various directions are reconstructed to generate a tomographic image. This allows generation of the tomographic image with high resolution in consideration of the error in repeated positioning.

In addition, the position detecting sensor is adopted to improve the insufficient repeated positioning accuracy. Such a simple configuration allows the apparatus at lower costs than a currently-used apparatus with a plurality of guiding units on every edge of a stage.

Moreover, it is preferable that the rotational fluctuation amount calculating unit of the radiation inspecting apparatus calculates the rotational fluctuation amount of the stage in accordance with the detected positional information from the position detecting sensor upon calibration of the stage drive unit with a calibration phantom and the detected positional information from the position detecting sensor upon the imaging of the inspection image. That is, the calibration is performed on a positioning accuracy of the stage drive unit with high repeat reproducibility using the calibration phantom. The position detecting sensor detects the positional information upon the calibration, and the rotational fluctuation amount caused by the inconstant attitude variation is calculated in accordance with the detected positional information upon the calibration and the detected positional information upon the imaging of the inspection object. This allows calculation of the rotational fluctuation amount more preciously than the case with an unknown positioning accuracy on one edge adjacent to a drive shaft.

Moreover, it is preferable in the radiation inspecting apparatus that the stage drive unit is disposed adjacent to a first edge of the stage, and the position detecting sensor is disposed adjacent to a second edge of the stage opposite to the first edge. That is, the stage drive unit faces to the position detecting sensor across the stage. This allows detection of the attitude variation of the stage in a wide range.

Moreover, in the radiation inspecting apparatus, the stage is moved in at least two directions along an X-axis and a Y-axis. The stage drive unit is provided along each of the X-axis and the Y-axis. The guiding units are disposed on edges of the stage in a direction orthogonal to a moving direction thereof, the guiding units guiding the stage in the moving direction. An additional guiding unit is disposed on one of the X-axis and the Y-axis in the direction orthogonal to the moving direction, and the position detecting sensor is provided on the other of the X-axis and the Y-axis. Such is preferable. The additional guiding unit is disposed on one of the X-axis and Y-axis. This achieves an enhanced restraint force of the stage in the yawing direction. Moreover, the position detecting sensor is disposed on the other of the X-axis and the Y-axis. This allows calculation of the stage shift amount in accordance with the detected positional information from the position detecting sensor.

Moreover, it is preferable in the radiation inspecting apparatus that the position detecting sensor is disposed on either the X-axis or the Y-axis in the moving direction in which a gap between the guiding unit on one of the edges of the stage and the stage drive unit on the other of the edges of the stage is larger. That is, the stage has a larger attitude variation on either the X-axis or the Y-axis in the moving direction in which the gap between the guiding unit and the stage drive unit is larger. Consequently, the attitude variation of the stage is detectable in a wide range with arrangement of the position detecting sensor. This allows calculation of the stage shift amount with high accuracy.

Moreover, it is preferable in the radiation inspecting apparatus that the stage is moved in at least two moving directions along the X-axis and the Y-axis, and the stage drive unit and the position detecting sensor are provided in each of the moving directions. This allows calculation of the stage shift amount with high accuracy in accordance with the detected positional information from the position detecting sensors in the moving directions.

Moreover, it is preferable that the radiation inspecting apparatus further includes an imaging system drive unit driving at least either the radiation source or the radiation detector. That is, when only the stage 2 is moved, a detector sometimes has difficulty in tracking an inspection object W at the same attention point continuously. That is because the FPD 4 has restriction in size of a detection area, and the attention point is out of the detection area of the FPD. Accordingly, not only the stage 2 but also an X-ray tube 3 or the FPD 4 is moved, whereby the attention point of the inspection object W can be continuously tracked without being out of the detection area of the FPD 4.

Moreover, another embodiment of the present invention discloses a radiation inspecting apparatus having a radiation source emitting radiation to an inspection object, a radiation detector detecting radiation passing through the inspection object to capture projection image, and a stage disposed between the radiation source and the radiation detector for supporting the inspection object placed thereon. The apparatus includes a stage drive unit moving the stage; a position detecting sensor detecting a position of the stage; a rotational fluctuation amount calculating unit calculating a rotational fluctuation amount of the stage around a power transmission part of the stage and the stage drive unit as a base point in accordance with detected positional information from the position detecting sensor upon imaging of the inspection object; a stage shift amount calculating unit calculating a stage shift amount in accordance with the rotational fluctuation amount and a distance between the base point and an imaging position, the stage shift amount representing a fluctuation amount of the stage at the imaging position; a pixel shift amount converting unit converting the stage shift amount into a pixel shift amount on the projection image; and a positional deviation correcting unit moving the projection image in accordance with the pixel shift amount in a direction in which a positional deviation is eliminated.

With the radiation inspecting apparatus according to the embodiment of the present invention, the rotational fluctuation amount of the stage is calculated around the power transmission part of the stage and the stage drive unit as the base point in accordance with the detected positional information from the position detecting sensor upon imaging of the inspection object. Then, the stage shift amount, representing the fluctuation amount of the stage at the imaging position, is calculated in accordance with the rotational fluctuation amount and the distance between the base point and the imaging position on the stage. Specifically, the stage shift amount at the imaging position is calculated from the rotational fluctuation amount of the stage around the base point and the distance between base point and the imaging position on the stage. Here, the stage shift amount corresponds to a positional deviation of the stage at the imaging position caused by the attitude variation of the stage in a yawing direction, and thus an error in repeated positioning. The stage shift amount is converted into the pixel shift amount on the projection image, and the projection image is moved in accordance with the converted pixel shift amount in the direction in which the positional deviation is eliminated. Consequently, a tracking function that always tracks the attention point of the inspection image at the center allows generation of the projection image positioned with high accuracy even when the repeated positioning accuracy is insufficient.

In addition, the present specification also discloses the following embodiment concerning the radiation inspecting apparatus.

(1) Another embodiment of the radiation inspecting apparatus according to the present invention. The radiation inspecting apparatus includes a guiding unit disposed on both edges of the stage in a direction orthogonal to a moving direction and guiding the stage in the moving direction. The stage drive unit also functions as the guiding unit on one of the both edges of the stage on the stage drive unit. This allows reduction in number of guiding units and production of an inexpensive and compact apparatus.

ADVANTAGEOUS EFFECTS OF INVENTION

With the radiation inspecting apparatus according to the embodiment of the present invention, the rotational fluctuation amount of the stage is calculated around the power transmission part of the stage and the stage drive unit as the base point in accordance with the detected positional information from the position detecting sensor upon capturing the inspection object. Then, the stage shift amount, representing the fluctuation amount of the stage at the imaging position, is calculated in accordance with the rotational fluctuation amount and the distance between the base point and the imaging position on the stage. That is, the stage shift amount at the imaging position is calculated from the rotational fluctuation amount of the stage around the base point and the distance between the base point and the imaging position on the stage. Here, the stage shift amount corresponds to a positional deviation of the stage at the imaging position caused by the attitude variation of the stage in a yawing direction, and thus an error in repeated positioning. This allows generation of a tomographic image with high resolution or a projection image positioned with high accuracy even when some inconstant attitude variation causes insufficient repeated positioning accuracy.

BRIEF DESCRIPTION OF DRAWINGS

For the purpose of illustrating the invention, there are shown in the drawings several forms which are presently preferred, it being understood, however, that the invention is not limited to the precise arrangement and instrumentalities shown.

FIG. 3 exemplarily illustrates a plan view of an attitude variation of the stage in a yawing direction.

FIG. 11 is a flow chart for illustrating operation of the X-ray inspecting apparatus.

DESCRIPTION OF EMBODIMENTS

<Embodiment 1>

Figure 1:
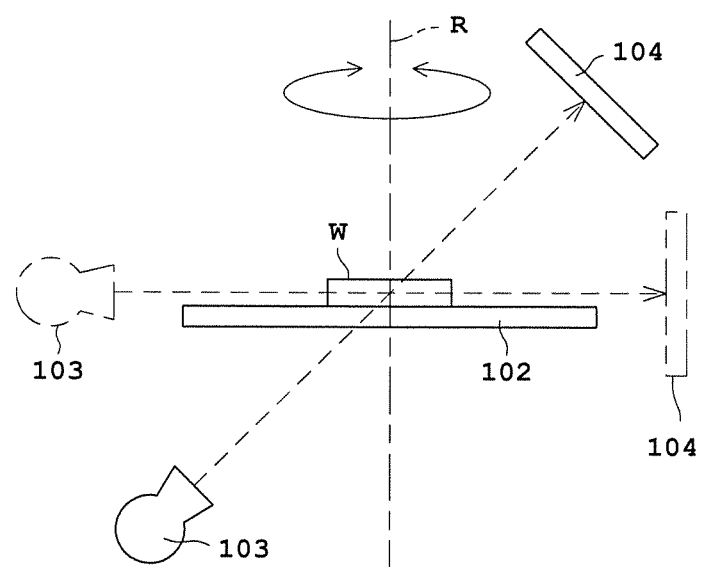
FIG. 1 illustrates a currently-used radiation detecting apparatus.
Figure 2A:
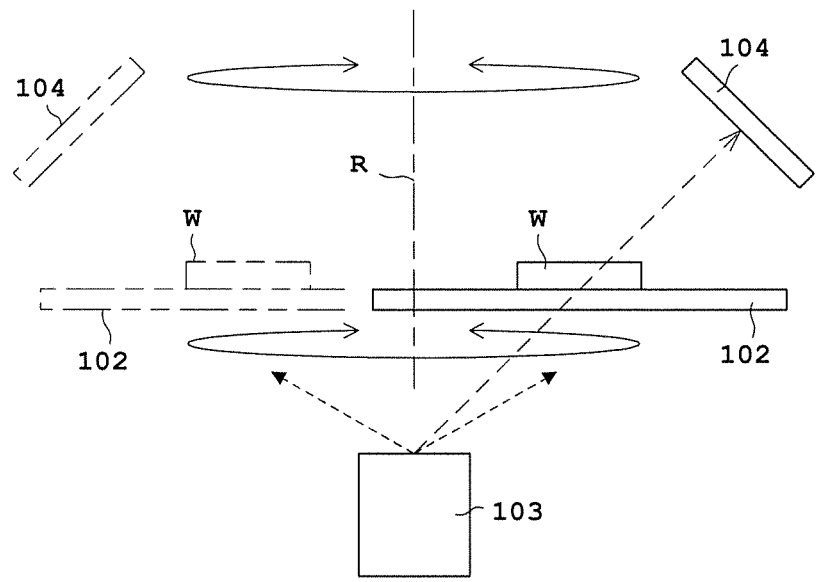
FIG. 2A illustrates a currently-used radiation detecting apparatus.
Figure 2B:
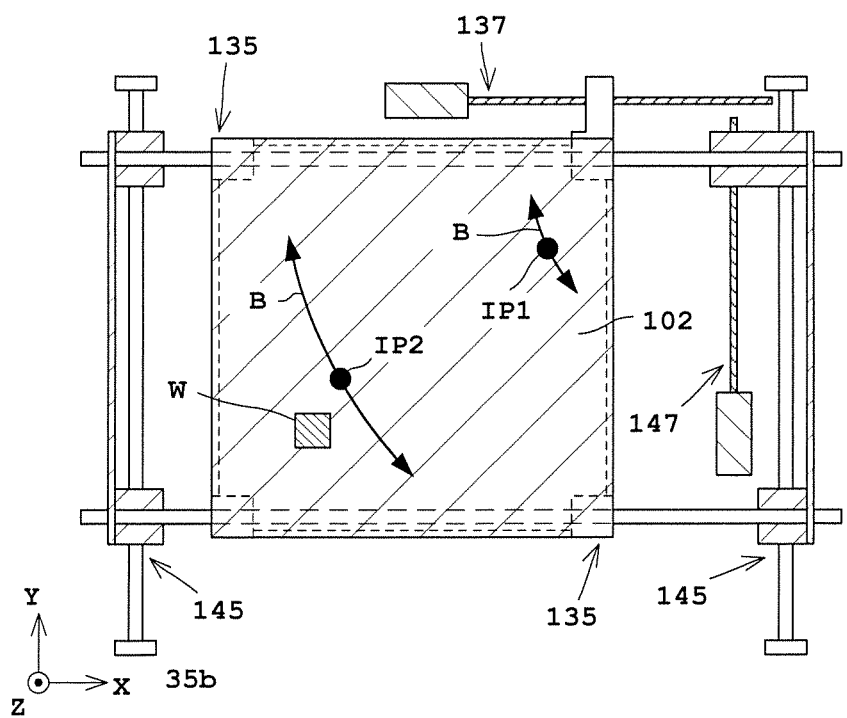
FIG. 2B is a plan view of a stage and its surroundings of the currently-used radiation detecting apparatus illustrated in FIG. 2A.
Figure 4:
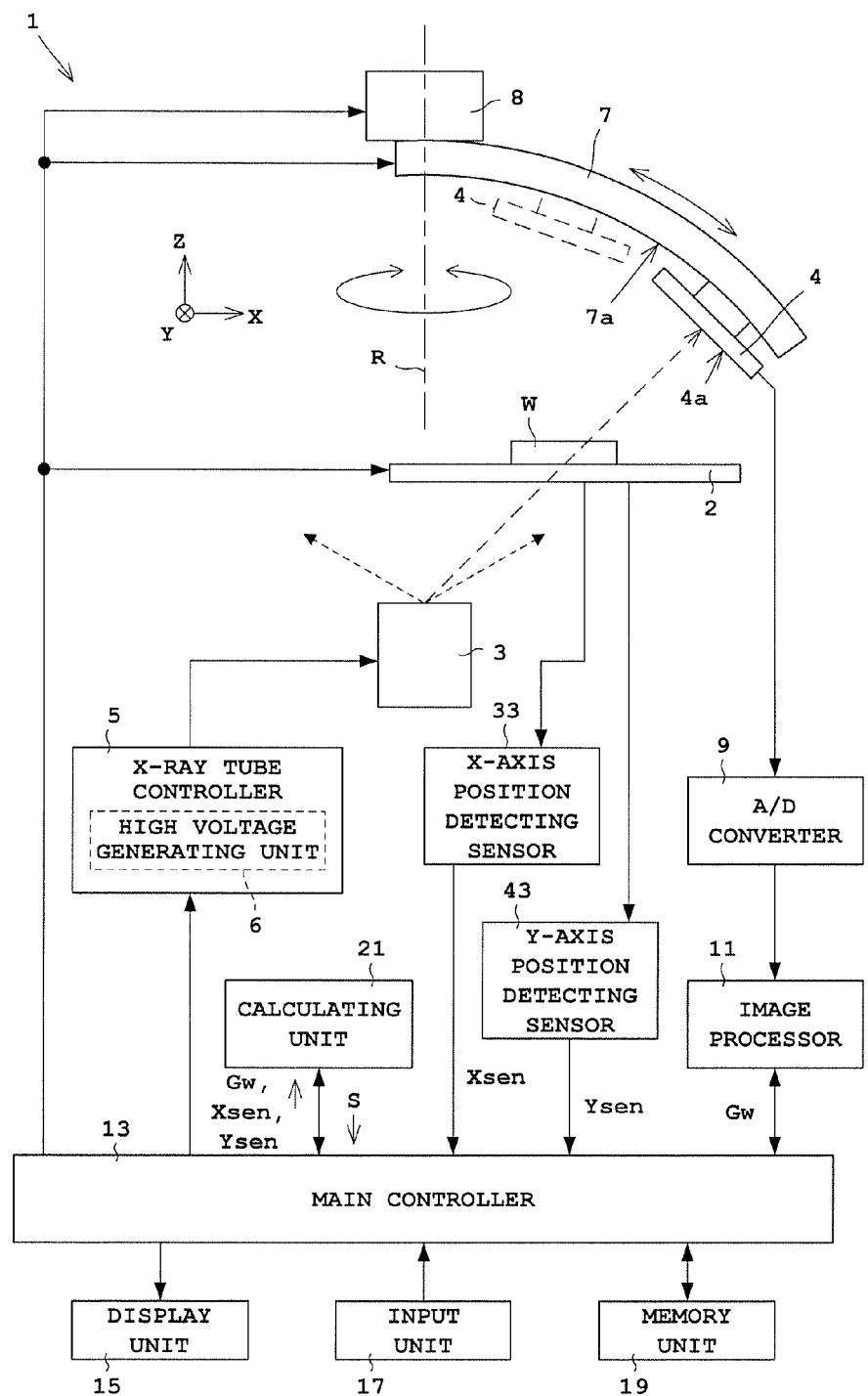
FIG. 4 schematically illustrates an X-ray inspecting apparatus according to one embodiment of the present invention.

The following describes Embodiment 1 of the present invention with reference to drawings. An X-ray inspecting apparatus is to be described as one example of the radiation inspecting apparatus. FIG. 4 schematically illustrates an X-ray inspecting apparatus of Embodiment 1.

Reference is made to FIG. 4. An X-ray inspecting apparatus 1 includes a stage 2, an X-ray tube 3 and a flat panel X-ray detector (hereinafter, referred to as an "FPD") 4. The stage 2 supports an inspection object W placed thereon. The X-ray tube 3 and the flat panel X-ray detector 4 face to each other across the stage 2 obliquely relative to a vertical direction (rotation axis R). Here, the X-ray tube 3 corresponds to the radiation source in the present invention. The FPD 4 corresponds to the radiation detector in the present invention.

The X-ray tube 3 is fixed so as not to move or rotate. The X-ray tube 3 emits X-rays upward vertically, thereby emitting X-rays to the inspection object W. The X-ray tube 3 is controlled by an X-ray tube controller 5. The X-ray tube controller 5 includes a high voltage generating unit 6 generating tube voltage and tube current of the X-ray tube 3. The X-ray tube controller 5 controls emission of X-rays from the X-ray tube 3 in accordance with X-ray irradiation conditions such as the tube voltage, the tube current and an irradiation time.

The FPD 4 has numerous X-ray detecting elements arranged in a two-dimensional matrix form on an X-ray detecting surface 4a thereof on which an X-ray fluoroscopic image of the inspection object W is projected. The X-ray detecting elements each convert X-rays into electric signals and detect the converted signals. Examples of the matrix of X-ray detecting elements include a several-thousand by several-thousand matrix. The X-ray detecting elements are each either a direct conversion film type of converting X-rays into electric signals directly or an indirect conversion film type of converting X-rays into light temporarily and further converting the light into electric signals. The X-ray detector 4 is not limited to an FPD. Alternatively, the X-ray detector 4 may be formed by an image intensifier and a camera.

The FPD 4 is movably supported by a detector tilting drive unit 7. As illustrated by solid lines or dotted lines, the detector tilting drive unit 7 tilts the detecting surface 4a of the FPD 4 by moving the FPD 4 along a curve portion 7a thereof. The FPD 4 is supported by a detector rotating mechanism 8 via the detector tilting drive unit 7. The detector rotating mechanism 8 rotates the FPD 4 about the rotation axis R.

The stage 2 is moved in an X-direction and a Y-direction. Correspondingly, the stage 2 is translated on an XY-plane orthogonal to the rotation axis R in circular orbit around the rotation axis R upon tomography. Here, the FPD 4 is rotated by the detector rotating mechanism 8 around the rotation axis R in synchronization with translation of the stage 2. Consequently, a plurality of projection images Gw of the inspection object W from different directions is obtained. The surroundings of the stage 2 are to be mentioned later.

An A/D converter 9, an image processor 11, and a main controller 13 are disposed on a subsequent stage of the FPD 4 in turn. The A/D converter 9 converts an analog X-ray detection signal into a digital X-ray detection signal. Here, the analog X-ray detection signal is one type of the projection image Gw outputted from the FPD 4. The image processor 11 performs a required processing such as log-transform to the digitally converted X-ray detection signal, and outputs the signal as the projection image Gw. The main controller 13 controls components of the X-ray inspecting apparatus 1 en bloc. The main controller 13 is formed by a central processing unit (CPU) and the like. The main controller 13 controls the detector tilting drive unit 7, the detector rotating mechanism 8, and X-axis and Y-axis stage drive units 37 and 47, to be mentioned later, for tomography.

The X-ray inspecting apparatus 1 further includes a display unit 15, an input unit 17, and a memory unit 19. The display unit 15 is formed by a monitor, and the like. The input unit 17 is formed by a keyboard, a mouse and the like. The memory unit 19 is formed by a storage medium including a demountable one such as a ROM (Read-only Memory), a RAM (Random-Access Memory), a hard disk, and the like.

The X-ray inspecting apparatus 1 further includes a calculating unit 21. The calculating unit 21 includes software or hardware, or a combination of these. The calculating unit 21 calculates stage shift amounts Δx and Δy at an imaging position IP, and changes a parameter PRc for image reconstruction using the calculated stage shift amounts Δx and Δy to generate a tomographic image S. Here, the stage shift amounts Δx and Δy represent positional deviations of the stage 2 resolved into the X-direction and the Y-direction, respectively, at the imaging position IP caused by an attitude variation of the stage 2 in a yawing direction B. That is, the stage shift amounts Δx and Δy are each variable depending on an imaging direction of tomography, and each correspond to an error in repeated positioning.

<Stage and its Surroundings>

Figure 5A:
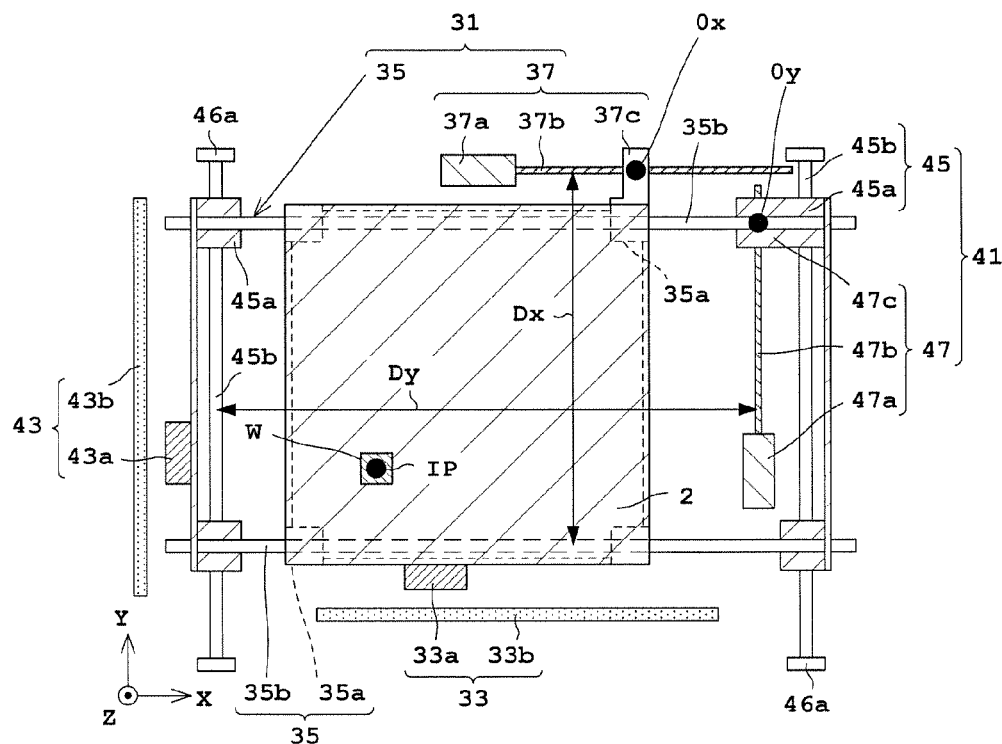
FIG. 5A is a plan view of the stage and its surroundings.
Figure 5B:
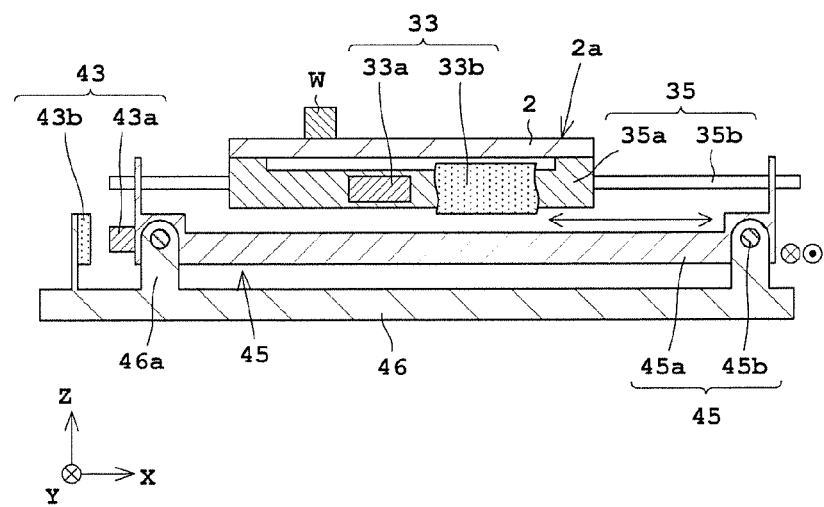
FIG. 5B is a side view of a configuration in FIG. 5A.

The following describes the stage 2 and its surroundings. The stage 2 is movable in the two directions along the X-axis and the Y-axis. A position detecting sensor is disposed in every moving direction. The position detecting sensors are disposed across the stage 2 opposite to the stage drive unit that drives the stage 2. Consequently, the attitude variation of the stage 2 is detectable in a wide range. Moreover, the position detecting sensors along the X-axis and the Y-axis detect positional information Xsen and Ysen, respectively. From the positional information Xsen and Ysen, the stage shift amounts Δx and Δy each representing the positional deviation of the stage 2 at the imaging position IP are calculated. FIG. 5A is a plan view of the stage and its surroundings. FIG. 5B is a side view of the configuration in FIG. 5A.

Firstly, the following describes an X-axis stage moving mechanism 31 moving the stage 2 in an X-axis direction, and an X-axis position detecting sensor 33. The X-axis stage moving mechanism 31 includes an X-axis guiding unit 35 and an X-axis stage drive unit 37.

The X-axis guiding unit 35 supports the stage 2 movably in the X-axis direction. That is, the X-axis guiding unit 35 is disposed on both edges of a placement surface 2a (see FIG. 5B) of the stage 2 relative to a Y-axis direction. The Y-axis direction is orthogonal to a moving direction of the stage 2 when the stage 2 is moved along the placement surface 2a of the stage 2 in the X-axis direction. Moreover, the X-axis guiding unit 35 guides the stage 2 in the moving direction in the X-axis direction. The X-axis guiding unit 35 is formed by a movable part 35a and a fixed part 35b. The movable part 35a supports the stage 2, and is movable relative to the fixed part 35b.

The X-axis stage drive unit 37 is disposed on a first edge of the stage 2, and moves the stage 2 in the X-axis direction. The X-axis stage drive unit 37 is formed by a motor 37a, a screw shaft 37b, and a nut 37c. The screw shaft 37b is engaged into the nut 37c. When the motor 37a is rotated, its rotation is transmitted to the screw shaft 37b. Here, the screw shaft 37b is engaged into the nut 37c. Correspondingly, the rotation of the screw shaft 37b is transmitted as drive of the stage 2 in the X-axis direction. The nut 37c is integrated with the movable part 35a of the X-axis guiding unit 35.

The X-axis position detecting sensor 33 is disposed on a second edge of the stage 2 opposite to the first edge, and detects positional information on the stage 2 in the X-axis direction. The X-axis position detecting sensor 33 is formed by a linear encoder, and includes an X-axis direction sensor head 33a and an X-axis direction scale 33b.

The following describes a Y-axis stage moving mechanism 41 moving the stage 2 in the Y-axis direction, and a Y-axis position detecting sensor 43. The Y-axis stage moving mechanism 41 includes a Y-axis guiding unit 45 and a Y-axis stage drive unit 47.

The Y-axis guiding unit 45 supports the stage 2 movably in the Y-axis direction via the X-axis guiding unit 35. The Y-axis guiding unit 45 is disposed on both edges of the placement surface 2a (see FIG. 5B) of the stage 2 relative to the X-axis direction. The X-axis direction is orthogonal to the moving direction of the stage 2. The Y-axis guiding unit 45 is formed by a movable part 45a and a fixed part 45b. The movable part 45a supports the fixed part 35b of the X-axis guiding unit 35, and is movable relative to the fixed part 45b. The fixed part 45b is held on a base 46 of a casing of the X-ray inspecting apparatus 1. In FIG. 5A, a plurality of movable parts 45a are illustrated separately. However, in actual, the movable parts 45a are integrated with a frame holder, not shown.

The Y-axis stage drive unit 47 is disposed on the first edge of the stage 2, and moves the stage 2 in the Y-axis direction. The Y-axis stage drive unit 47 is formed by a motor 47a, a screw shaft 47b, and a nut 47c. The screw shaft 47b and the nut 47c are each formed by a ball screw, for example.

The Y-axis position detecting sensor 43 is disposed on the second edge of the stage 2 opposite to the first edge, and detects positional information on the stage 2 in the Y-axis direction. The X-axis position detecting sensor 43 is formed by a linear encoder, and includes an X-axis direction sensor head 43a and an X-axis direction scale 43b.

In FIG. 5B, the base 46 includes a holder 46a holding the fixed part 45b of the Y-axis guiding unit 45. The base 46 further has a Y-axis direction scale 43b of the Y-axis position detecting sensor 43 attached thereto. Here, the X-axis direction scale 33b is partially illustrated for convenience.

Figure 6:
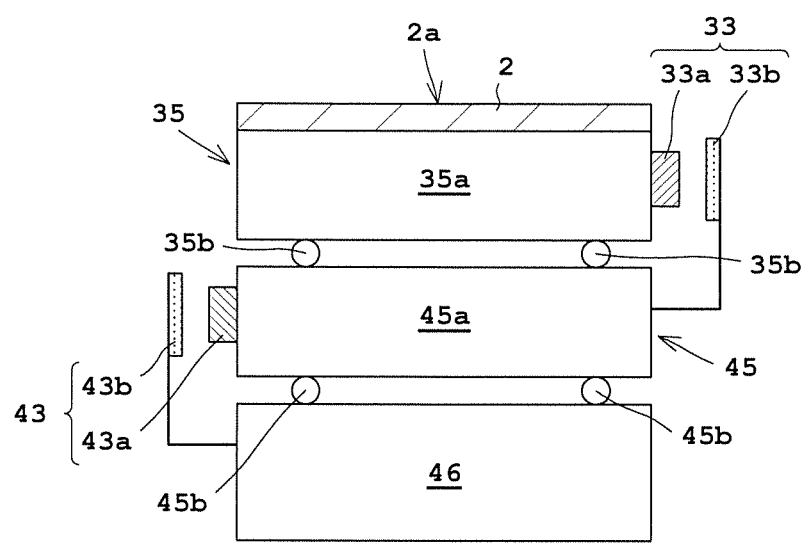
FIG. 6 illustrates the stage in a height direction and arrangement of X-axis and Y-axis position detecting sensors.

FIG. 6 is a schematic view of the configuration of the stage 2 in a height direction (Z-direction) and arrangement of the X-axis and Y-axis position detecting sensors 33 and 43. As illustrated in FIG. 6, the Y-axis guiding unit 45 (Y-axis stage moving mechanism 41), the X-axis guiding unit 35 (X-axis stage moving mechanism 31), and the stage 2 are disposed on the base 46 in this order. When the stage 2 is moved to any position, the X-axis position detecting sensor 33 determines a relative positional relationship between the movable part 35a and the fixed part 35b of the X-axis guiding unit 35. Here, the fixed part 35b of the X-axis guiding unit 35 is integrated with the movable part 45a of the Y-axis guiding unit 45. The fixed part 45b of the Y-axis guiding unit 45 is integrated with the base 46. The X-axis direction sensor head 33a is attached to the movable part 35a. The X-axis direction scale 33b is attached to the movable part 45a. The Y-axis direction sensor head 43a is attached to the movable part 45a. The Y-axis direction scale 43b is attached to the base 46.

Here, the X-axis guiding unit 35 and the Y-axis guiding unit 45 correspond to the guiding unit in the present invention. The X-axis stage drive unit 37 and the Y-axis stage drive unit 47 correspond to the stage drive unit in the present invention. The X-axis position detecting sensor 33 and the Y-axis position detecting sensor 43 correspond to the position detecting sensor in the present invention.

<Calculating Unit>

Figure 7:
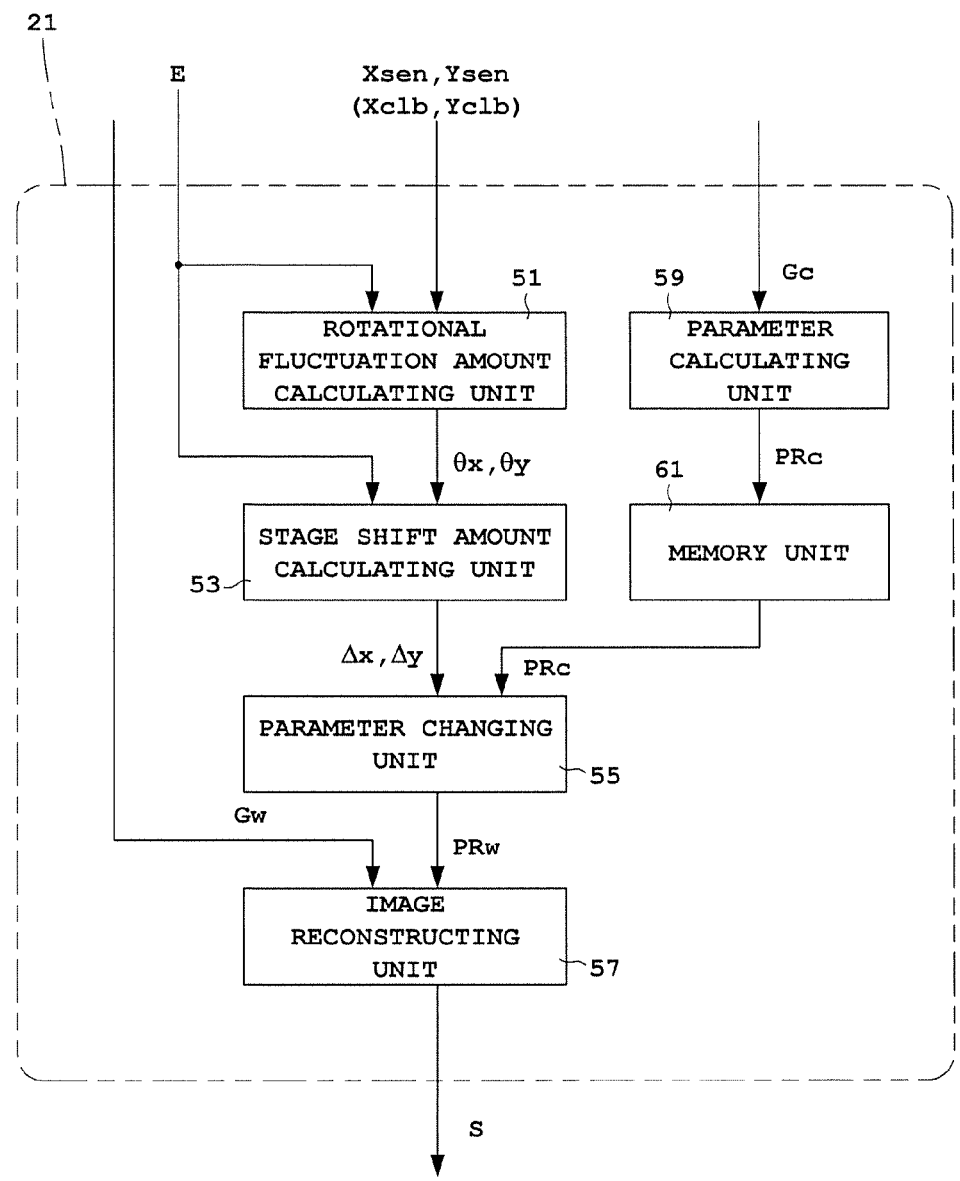
FIG. 7 illustrates a calculating unit.

The following describes the calculating unit 21. FIG. 7 illustrates the calculating unit 21. The calculating unit 21 includes a rotational fluctuation amount calculating unit 51, and a stage shift amount calculating unit 53. The rotational fluctuation amount calculating unit 51 calculates rotational fluctuation amounts (also referred to as attitude fluctuation amounts) θx and θy at X-axis and Y-axis sliding parts 0x and 0y (see FIG. 5A) as base points, respectively, in accordance with the detected positional information Xsen and Ysen detected by the X-axis and Y-axis position detecting sensors 33 and 43, respectively. The stage shift amount calculating unit 53 calculates stage shift amounts Δx and Δy at any imaging position IP on the stage 2 (e.g., an attention point of the inspection object) in accordance with the rotational fluctuation amounts θx and θy. Moreover, the calculating unit 21 further includes a parameter changing unit 55, and an image reconstructing unit 57. The parameter changing unit 55 changes a geometrical parameter PRc in accordance with the calculated stage shift amounts Δx and Δy. The geometrical parameter PRc is used upon reverse projection calculation of the two-dimensional image to a three-dimensional space for generating a tomographic image S in image reconstruction. The image reconstructing unit 57 generates the tomographic image S in consideration with the stage shift amounts Δx and Δy of the stage 2 at the imaging position IP for every tomography by performing coordinate conversion in accordance with the changed parameter PRw.

The X-axis sliding part 0x in FIG. 5A is a power transmission part between the stage 2 and the X-axis stage drive unit 37. Specifically, the X-axis sliding part 0x is a part where the screw shaft 37b of the X-axis stage drive unit 37 is engaged into the nut 37c integrated with the movable part 35a supporting the stage 2. Similarly, the Y-axis sliding part 0y is a part where the screw shaft 47b is engaged into the nut 47c.

<<Rotational Fluctuation Amount Calculating Unit>>

The following firstly describes the rotational fluctuation amount calculating unit 51. The rotational fluctuation amount calculating unit 51 calculates the rotational fluctuation amounts θx and θy around the power transmission part between the stage 2 and the X-axis and Y-axis stage drive units 33 and 43 as the base point, i.e., the X-axis and Y-axis sliding parts 0x and 0y, in accordance with the positional information Xsen and Ysen detected by the X-axis and Y-axis position detecting sensors 33 and 43, respectively, upon imaging of the inspection object W. The rotational fluctuation amounts θx and θy are each calculated from the following Equation (1). Here, FIGS. 8A and 8B are each an explanatory view of calculating the rotational fluctuation amounts θx and θy, respectively.

Figure 8A:
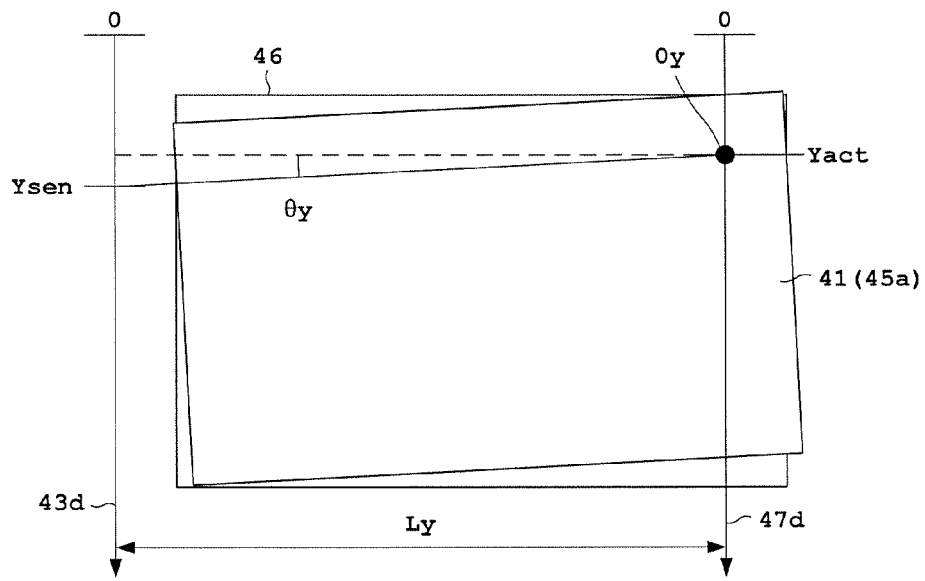
FIGS. 8A and 8B are each an explanatory view for a method of calculating a rotational fluctuation amount.
Figure 8B:
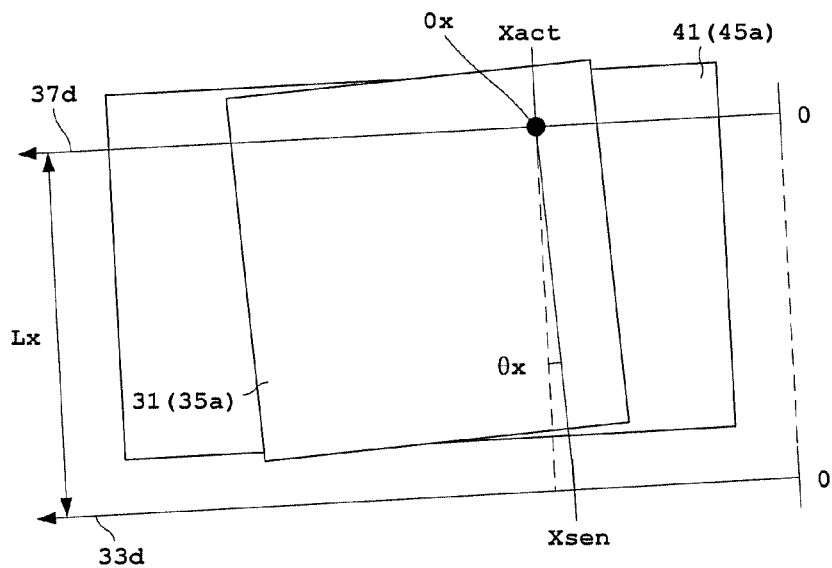

FIGS. 8A and 8B illustrate lines of extending loci of detecting parts in heads of the X-axis and Y-axis direction sensor 33a and 43a denoted by numerals 33d and 43d, respectively. Here, each of the loci is considered as a sensor axis. Accordingly, the numeral 33d denotes an axis of the X-axis direction sensor. The numeral 43d denotes an axis of the Y-axis direction sensor. Moreover, the numerals 37d and 47d illustrate lines of extending loci of the X-axis and Y-axis sliding parts 0x and 0y on the screw shafts 37b and 47b, respectively. Here, the lines are each considered as a drive axis. Accordingly, the numeral 37d denotes an X-axis direction drive axis, and the numeral 47d denotes a Y-axis direction drive axis. The same is applied to FIG. 9 to be mentioned later.

$$\theta_y = \tan^{-1}\left(\frac{(Y_{sen} - Y_{act})}{L_y}\right) \approx \frac{Y_{sen} - Y_{act}}{L_y} \quad (1)$$

$$\theta_x = \tan^{-1}\left(\frac{(X_{sen} - X_{act})}{L_x}\right) \approx \frac{X_{sen} - X_{act}}{L_x}$$

where Yact is a position of the Y-axis sliding part 0y in the Y-axis direction, Ysen is a detected position by the Y-axis position detecting sensor 43, Xact is a position of the X-axis sliding part 0x in the X-axis direction, Xsen is a detected position by the X-axis position detecting sensor 33, Ly is a distance between the Y-axis direction sensor axis 43d and the Y-axis direction drive axis 47d, and Lx is a distance between the X-axis direction sensor axis 33d and the X-axis direction drive axis 37d.

Equation (1) expresses a calculation method when positions of the X-axis and Y-axis sliding parts 0x and 0y by the X-axis and Y-axis stage drive units 33 and 43 are each known. That is, the above is a calculation method when command positions upon moving the X-axis and Y-axis sliding parts 0x and 0y to a preset position conform to actual positions of the X-axis and Y-axis sliding parts 0x and 0y, respectively. For instance, it is assumed that no calibration is performed on the X-axis and Y-axis stage drive units 33 and 43, and thus positioning accuracy itself of the X-axis and Y-axis stage drive units 33 and 43 is sometimes insufficient. In this case, an error caused by no calibration may occur even with sufficient repeated positioning accuracy. Consequently, the rotational fluctuation amounts θx and θy with high accuracy cannot be calculated.

Accordingly, the rotational fluctuation amounts θx and θy may be calculated from the following Equation (2). That is, detected positional information (sensor value) Xclb and Yclb by the X-axis and Y-axis position detecting sensors 35 and 45, respectively, is stored and used. The detected positional information (sensor value) Xclb and Yclb is obtained upon calibration of the positioning accuracy of the X-axis and Y-axis stage drive units 33 and 43 using a calibration phantom.

Here, the calibration is performed in the same radiography condition as the tomography of the inspection object W. That is, in the calibration, the stage 2 and the FPD 4 are each driven in the same orbit, and imaging is performed in the same direction as that in the tomography of the inspection object W. The detected positional information Xclb and Yclb in various imaging directions upon the calibration is stored in the memory unit 19. Here, the calibration causes enhanced positioning accuracy of the X-axis and Y-axis stage drive units 33 and 43, but causes no enhanced repeated positioning accuracy.

Figure 9A:
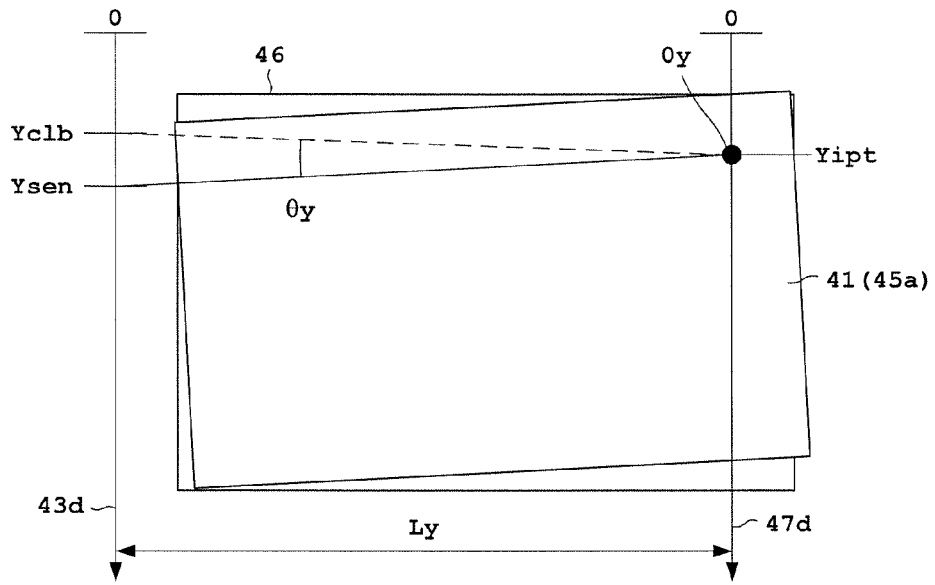
FIGS. 9A and 9B each explanatorily illustrate a method of calculating a rotational fluctuation amount with detected positional information upon calibration.
Figure 9B:
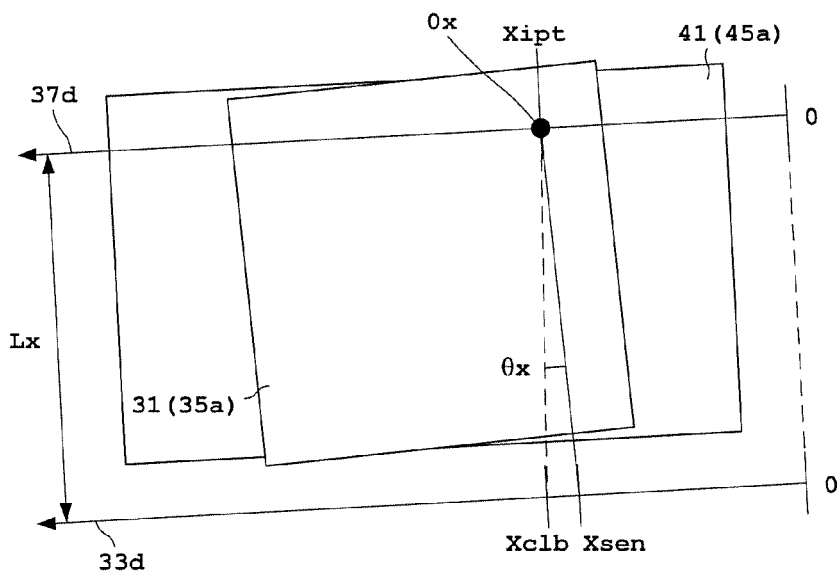

The rotational fluctuation amount calculating unit 51 calculates the rotational fluctuation amounts θx and θy in accordance with the detected positional information Xclb and Yclb upon the calibration, the detected positional information Xsen and Ysen upon imaging the inspection object W, and the command (set) positions Xipt and Yipt. FIGS. 9A and 9B are each an explanatory view of calculating the rotational fluctuation amounts θx and θy using the detected positional information Xclb and Yclb upon the calibration.

$$\theta_y = \tan^{-1}\left(\frac{Y_{sen} - Y_{ipt}}{L_y}\right) - \tan^{-1}\left(\frac{Y_{clb} - Y_{ipt}}{L_y}\right) \quad (2)$$

$$\approx \frac{Y_{sen} - Y_{ipt}}{L_y} - \frac{Y_{clb} - Y_{ipt}}{L_y}$$

$$= \frac{Y_{sen} - Y_{clb}}{L_y}$$

$$\theta_x = \tan^{-1}\left(\frac{X_{sen} - X_{ipt}}{L_x}\right) - \tan^{-1}\left(\frac{X_{clb} - X_{ipt}}{L_x}\right)$$

$$\approx \frac{X_{sen} - X_{ipt}}{L_x} - \frac{X_{clb} - X_{ipt}}{L_x}$$

$$= \frac{X_{sen} - X_{clb}}{L_x}$$

where Yipt is a command position (value) given to the Y-axis stage drive unit 47, Ysen is a detected position upon imaging the inspection object when the command position Yipt is given to the Y-axis stage drive unit 47, Yclb is a detected position upon the calibration when the command position Yipt is given to the Y-axis stage drive unit 47, Xipt is a command position given to the X-axis stage drive unit 37, Xsen is a detected position upon imaging the inspection object W when the command position Xipt is given to the X-axis stage drive unit 37, Xclb is a detected position upon calibration when the command position Xipt is given to the X-axis stage drive unit 37, Ly is a distance between the Y-axis direction sensor axis 43*d* and the Y-axis direction drive axis 47*d*, and Lx is a distance between the X-axis direction sensor axis 33*d* and the X-axis direction drive axis 37*d*.

<<Stage Shift Amount Calculating Unit>>

Figure 10A:
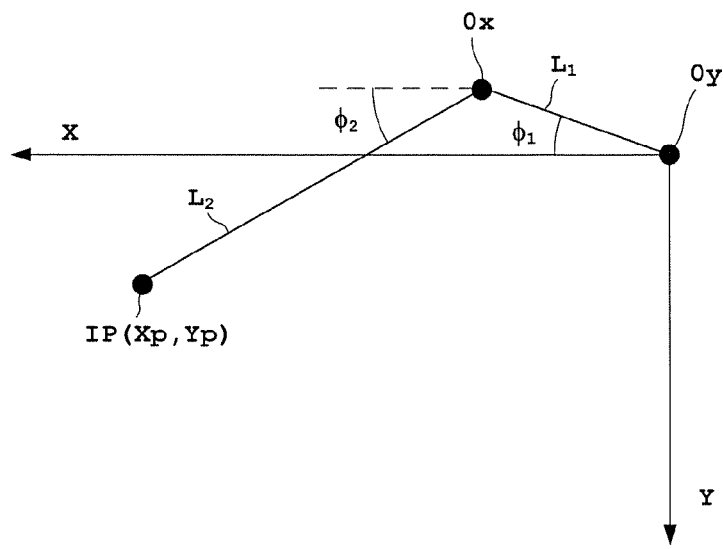
FIG. 10A is a schematic view used for explanation of calculating the stage shift amount with no rotational fluctuation amount.
Figure 10B:
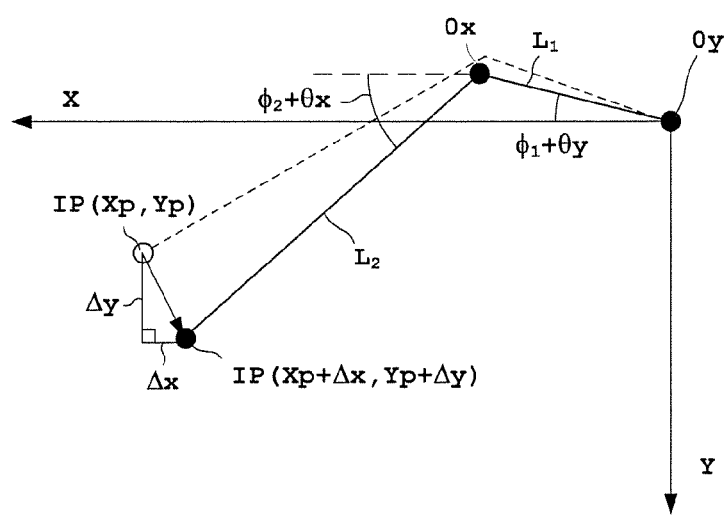
FIG. 10B is a schematic view used for explanation of calculating the stage shift amount in consideration with the rotational fluctuation amount.

The following describes the stage shift amount calculating unit 53. The stage shift amount calculating unit 53 calculates stage shift amounts Δx and Δy, representing the fluctuation amount of the stage 2 at the preset imaging position IP, in accordance with the rotational fluctuation amounts θx and θy, and a distance $L_2$ between the X-axis sliding part (base point) 0x and the imaging position IP. As illustrated in the schematic view of FIG. 10A, the stage shift amounts Δx and Δy can be calculated from the same concept as a "two-degree-of-freedom link mechanism". That is, the Y-axis sliding part 0y is considered as an original point of a link, the X-axis sliding part 0x as a node of the link, and an ideal imaging position IP(Xp,Yp) as a tip of the link. Accordingly, the stage shift amounts Δx and Δy of the stage 2 at the imaging position IP (Xp,Yp) can be calculated from the following Equation (3). FIG. 10A is a schematic view used for explanation of calculating the stage fluctuation amounts Δx and Δy with no rotational fluctuation amount. FIG. 10B is a schematic view used for explanation of calculating the stage shift amounts Δx and Δy in consideration with the rotational fluctuation amounts θx and θy. The stage shift amounts Δx and Δy are positional deviations of the stage 2 in the X-axis and Y-axis directions at the imaging position IP caused by the attitude variation of the stage 2 in the yawing direction B.

$$\begin{bmatrix} \Delta x \\ \Delta y \end{bmatrix} = \begin{bmatrix} L_1\cos(\phi_1 + \theta_x) + L_2\cos(\phi_2 + \theta_y) \\ L_1\sin(\phi_1 + \theta_x) + L_2\sin(\phi_2 + \theta_y) \end{bmatrix} - \begin{bmatrix} L_1\cos(\phi_1) + L_2\cos(\phi_2) \\ L_1\sin(\phi_1) + L_2\sin(\phi_2) \end{bmatrix} \quad (3)$$

$$\approx \begin{bmatrix} -L_1\sin(\phi_1)\cdot\theta_x - L_2\sin(\phi_2)\cdot\theta_y \\ L_1\cos(\phi_1)\cdot\theta_x + L_2\cos(\phi_2)\cdot\theta_y \end{bmatrix}$$

where $\phi_1$(Xact) is an angle which the Y-axis sliding part 0y forms with the X-axis sliding part 0x with no rotational fluctuation amount, $\phi_2$(Xp, Xp) is an angle which the X-axis sliding part 0x forms with the imaging position IP with no rotational fluctuation amount, $L_1$(Xact) is a distance between the Y-axis sliding part 0y and the X-axis sliding part 0x, and $L_2$(Xp, Xp) is a distance between the X-axis sliding part 0x and the imaging position IP.

In FIG. 7, the numeral E denotes a radiography condition. Here, the information other than the detected position information Xsen and Ysen, such as Xact, Yact, Lx, and Ly, that is adopted in the above Equations (1) to (3) (also in the Equation (5) to be mentioned later) is given as the radiography condition. The detected position information Xsen and Ysen is detected by the X-axis and Y-axis position detecting sensors 33 and 43.

<<Parameter Converting Unit>>

The following describes the parameter changing unit 55. A tomographic image S is calculated with a known image reconstruction method, such as an FBP method to be mentioned later. For calculation of the image reconstruction, a process such as projection or reverse projection is conducted. At this time, a geometrical position relationship between a coordinate of the three-dimensional space such as the inspection object W and a coordinate of a two-dimensional image such as a projection image Gw of the FPD 4 should be recognized accurately. Such a positional condition is referred to as a "geometrical conversion condition" appropriately. The geometrical conversion condition is composed by a plurality of parameters. The parameters are to be described as a parameter PR for convenience of explanation.

The parameter PRc is calculated by a parameter calculating unit 59 upon the calibration with the calibration phantom. The following describes in detail a method of calculating the parameter PRc prior to change. A phantom having a ball marker of a high-X-ray absorber (e.g., metal) inside thereof is used for the calibration phantom. Such a calibration phantom is imaged in various directions, whereby a plurality of projection images Gc is obtained. The parameter calculating unit 59 calculates various parameters PRc in accordance with coordinates of the markers contained in the projection images Gc and the coordinate of the marker in the calibration phantom. The calculated parameters PRc are stored in a memory unit 61. Here, the parameters PRc are not necessarily stored in the memory unit 61 but may be stored in the memory unit 19.

On the other hand, when the image reconstruction is performed with the parameters PRc directly, the tomographic image S becomes unclear since the error in repeated positioning of the stage 2 mentioned above, i.e., rattle of the stage 2 is not considered. Accordingly, for obtaining the parameters PRw, the parameter changing unit 55 changes the parameters PRc in accordance with the stage shift amounts Δx and Δy as the positional deviations of the stage 2 in the X-axis and Y-axis directions at the imaging position IP caused by the attitude variation of the stage 2 in the yawing direction B.

The following firstly describes a concrete geometrical conversion condition with the parameters PRc. The geometrical conversion condition is, for example, typically indicated with the following Equations (4) expressing a fluoroscopy projection from the three-dimensional space to the two-dimensional image as well as the parameters PRc contained in the Equations (4).

$$\tilde{P}_{ip} = \lambda APM\tilde{P}_w \quad (4)$$

$$\tilde{P}_w = [\; X_w \quad Y_w \quad Z_w \quad 1\; ]^T$$

$$\tilde{P}_{ip}[\; x_{ip} \quad y_{ip} \quad 1\; ]^T$$

$$M = \begin{bmatrix} R & t \\ 0 & 1 \end{bmatrix}$$

$$P = \begin{bmatrix} f & 0 & 0 & 0 \\ 0 & f & 0 & 0 \\ 0 & 0 & 1 & 0 \end{bmatrix}$$

$$A = \begin{bmatrix} k_x & \text{skew} & \sigma_x \\ 0 & k_y & \sigma_y \\ 0 & 0 & 1 \end{bmatrix}$$

where $\tilde{P}$ w is a three-dimensional homogeneous coordinate in a world coordinate system, $\tilde{P}$ ip is a two-dimensional homogeneous coordinate in a pixel coordinate system on an image, M is a transformation matrix (R: rotation matrix, t: translation vector), P is a transformation matrix, and A is a transformation matrix.

The transformation matrix M indicates a positional relationship between a coordinate system (world coordinate system) of the inspection object W in a three-dimensional space and the coordinate system of a focus of the X-ray tube 3. This indicates the degree of translation and rotation of the coordinate of the inspection object W for conforming to the coordinate of a focus of the X-ray tube 3. The transformation matrix P is used for transforming the coordinate system of the focus of the X-ray tube 3 into the coordinate system of the FPD 4. A parameter f in the transformation matrix P indicates a distance between the focus of the X-ray tube 3 and a surface of the FPD 4. The transformation matrix A is used for transforming the coordinate system of the FPD 4 into the coordinate system in the two-dimensional image. With the transformation matrixes M, P, and A, the coordinate system of the inspection object W in the three-dimensional space is transformed into the coordinate system in the two-dimensional image.

In the Equation (4), the parameter changing unit 55 substitutes the stage shift amounts Δx and Δy into the parameter t in the transformation matrix M appropriately. This obtains a parameter PRw in consideration of the stage shift amounts Δx and Δy as the errors in repeated positioning.

That is, the parameter changing unit 55 changes the parameter PRc in the geometrical conversion condition indicating the geometrical relationship upon calculation of the reverse projection from the two-dimensional image to the three-dimensional space in accordance with the stage shift amounts Δx and Δy. This allows accurate coordinate transformation from the three-dimensional space to the two-dimensional image with the Equation (4) or that from the two-dimensional image to the three-dimensional space with another equation other than the Equation (4). This also achieves an improved influence of the parameters PRc caused by the rattle of the stage 2, the parameters PRc being different individually depending on various imaging directions for tomography and the preset imaging position IP on the stage 2.

<<Image Reconstructing Unit>>

The following describes the image reconstructing unit 57. The image reconstructing unit 57 reconstructs a plurality of projection images Gw of the inspection object W obtained from various directions in accordance with the geometrical conversion condition containing the parameters PRw changed by the parameter changing unit 55, thereby generating a tomographic image S. A well-known method, such as an FBP (Filtered Back Projection) method, is used as an algorithms of the image reconstruction. An ML-EM (maximum likelihood-expectation maximization) method is included as another example of the well-known method.

The following describes operation of the X-ray inspecting apparatus 1 with reference to a flow chart in FIG. 11. Steps S11 and S12 are to be described along with the Step S04.

[Step S01] Tomography of Inspection Object

Reference is made to FIG. 4. The X-ray tube 3 fixedly disposed emits X-rays broadly upward vertically, thereby emitting X-rays to the inspection object W. The FPD 4 detects X-rays passing through the inspection object W to obtain projection images Gw. Here, tomography is conducted on the inspection object W from various directions, whereby a plurality of projection images Gw is obtained. In addition, the stage 2 supporting the inspection object W placed thereon is translated by the X-axis and Y-axis stage moving mechanisms 31 and 41 around the rotation axis R in circular orbit on an X-Y plane orthogonal to the rotation axis R during tomography. Moreover, the FPD 4 is rotated by the detector rotating mechanism 8 around the rotation axis R in synchronization with the translation of the stage 2.

In the various directions for tomography, the projection images Gw are captured, and the detected positional information Xsen and Ysen of the stage 2 by the X-axis and Y-axis position detecting sensors 33 and 43, respectively, is detected. The detected positional information Xsen and Ysen detected by the X-axis and Y-axis position detecting sensors 33 and 43 is sent to the calculating unit 21.

[Step S02] Calculation of Rotational Fluctuation Amount

The rotational fluctuation amount calculating unit 51 calculates the rotational fluctuation amounts θx and θy around the power transmission part of the stage 2 and the X-axis and Y-axis stage drive units 33 and 43 as the base points, i.e., the X-axis and Y-axis sliding parts 0x and 0y, in accordance with the detected positional information Xsen and Ysen detected by the X-axis and Y-axis position detecting sensors 33 and 43 upon imaging the inspection object W. The rotational fluctuation amounts θx and θy are calculated by the Equation (1), (2), or (5) to be mentioned later. In the Equation (2), the detected positional information Xclb and Yclb in various imaging directions is used that is detected and stored during the tomography upon the calibration in the Step S11.

[Step S03] Calculation of Stage Shift Amount

The stage shift amount calculating unit 53 calculates the stage shift amounts Δx and Δy, each representing the fluctuation amount of the stage 2 at the imaging position IP preset on the stage 2, in accordance with the rotational fluctuation amounts θx and θy and distances $L_1$ and $L_2$ between the X-axis sliding part (base point) 0x and the imaging position IP.

[Step S04] Change of Parameter

The parameter changing unit 55 changes a translation vector t (parameter) in the transformation matrix M in the geometrical conversion condition representing a geometrical relationship between the three-dimensional space and the two-dimensional image in accordance with the stage shift amounts Δx and Δy. That is, the parameter PRc is changed into the parameter PRw.

The parameter PRc in the geometrical conversion condition prior to changing is calculated upon the calibration with the calibration phantom. Firstly, the calibration phantom is imaged from various directions, whereby a plurality of projection images Gc is obtained (Step S11). Then, the parameter calculating unit 59 calculates a parameter PRc in accordance with the coordinate of the marker in each of the projection image Gc and the coordinate of the marker in the calibration phantom (Step S12). The calculated parameter PRc is stored in the memory unit 61.

[Step S05] Image Reconstruction

The image reconstructing unit 57 reconstructs the projection images Gw of the inspection object W captured from various directions in accordance with the geometrical conversion condition of the parameter PRw changed by the parameter changing unit 55, thereby generating a tomographic image S. The generated tomographic image S is displayed on the display unit 15, and is stored in the memory unit 19. The tomographic image S has high resolution since it is reversely projected at an accurate position with a suppressed positional deviation in consideration with the stage shift amounts Δx and Δy.

In the present embodiment, the rotational fluctuation amounts θx and θy of the stage 2 around the power transmission parts of the stage 2 and the X-axis and Y-axis stage drive units 37 and 47 as the base point, i.e., at the X-axis and Y-axis sliding parts 0x and 0y, is calculated in accordance with the detected positional information Xsen and Ysen detected by the X-axis and Y-axis position detecting sensors 35 and 45 upon imaging of the inspection object W. Then, the stage shift amounts Δx and Δy representing the shift amount of the stage 2 at the imaging position IP is calculated in accordance with the rotational fluctuation amounts θx and θy as well as the distances $L_1$ and $L_2$ between the base points (X-axis and Y-axis sliding parts 0x and 0y) and the imaging position IP on the stage 2, respectively. That is, the stage shift amounts Δx and Δy at the imaging position IP are calculated from the rotational fluctuation amounts θx and θy of the stage 2 around the base points (X-axis and Y-axis sliding part 0x and 0y) and the distances $L_1$ and $L_2$ between the base points (X-axis and Y-axis sliding parts 0x and 0y) and the imaging position IP on the stage 2. Here, the stage shift amounts Δx and Δy are each a positional deviation of the stage 2 at the imaging position IP in the X-axis and Y-axis directions caused by the attitude variation of the stage 2 in the yawing direction B. Accordingly, the stage shift amounts correspond to errors in repeated positioning. Then, the positional deviation of the stage 2 is corrected in accordance with the stage shift amounts Δx and Δy, and the projection images Gw of the inspection object W from various directions are reconstructed to generate the tomographic image S. As a result, the tomographic image S with high resolution in consideration of the errors in repeated positioning can be generated.

In addition, a simple configuration of adopting the X-axis and Y-axis position detecting sensors 37 and 47 is merely required to improve the insufficient repeated positioning accuracy. Consequently, the apparatus is obtainable whose cost is lower than the currently-used apparatus with a plurality of X-axis and Y-axis guiding units on both edges of the stage 2.

Moreover, the rotational fluctuation amount calculating unit 51 calculates the rotational fluctuation amounts θx and θy in accordance with the detected positional information Xclb and Yclb of the X-axis and Y-axis position detecting sensors 33 and 43, respectively, detected upon the calibration with the calibration phantom, and the detected positional information Xsen and Ysen detected by the X-axis and Y-axis position detecting sensors 33 and 43, respectively, upon imaging of the inspection object W. That is, the calibration is performed on the X-axis and Y-axis stage drive units 37 and 47 with the calibration phantom. Accordingly, a satisfied positioning accuracy of the stage 2 moved by the X-axis and Y-axis stage drive units 37 and 47 is obtainable. Upon the calibration, the X-axis and Y-axis position detecting sensors 33 and 43 detect the detected positional information Xclb and Yclb. Then the rotational fluctuation amounts θx and θy are calculated in accordance with the detected positional information Xclb and Yclb upon the calibration and the detected positional information Xsen and Ysen upon imaging of the inspection object W. This achieves accurate calculation of the rotational fluctuation amounts θx and θy with the satisfied positioning accuracy of the stage 2.

Moreover, the X-axis and Y-axis stage drive units 37 and 47 are each disposed on a first edge of the stage 2, and the X-axis and Y-axis position detecting sensors 33 and 43 are each disposed on a second edge of the stage 2, the first and second edges facing to each other. That is, the stage drive unit faces to the position detecting sensor across the stage. This allows detection of the attitude variation of the stage in a wide range.

Moreover, the stage is moved in the two directions of the X-direction and the Y-direction. The X-axis and Y-axis stage drive units 37 and 47 and the X-axis and Y-axis position detecting sensors 33 and 43 are provided in the moving directions of the X-direction and the Y-direction, respectively. This allows calculation of the stage moving amounts Δx, Δy with high accuracy in accordance with the detected positional information Xsen and Ysen detected by the X-axis and Y-axis position detecting sensors 33 and 43 in the moving directions of the X-direction and the Y-direction.

<Embodiment 2>

Figure 12:
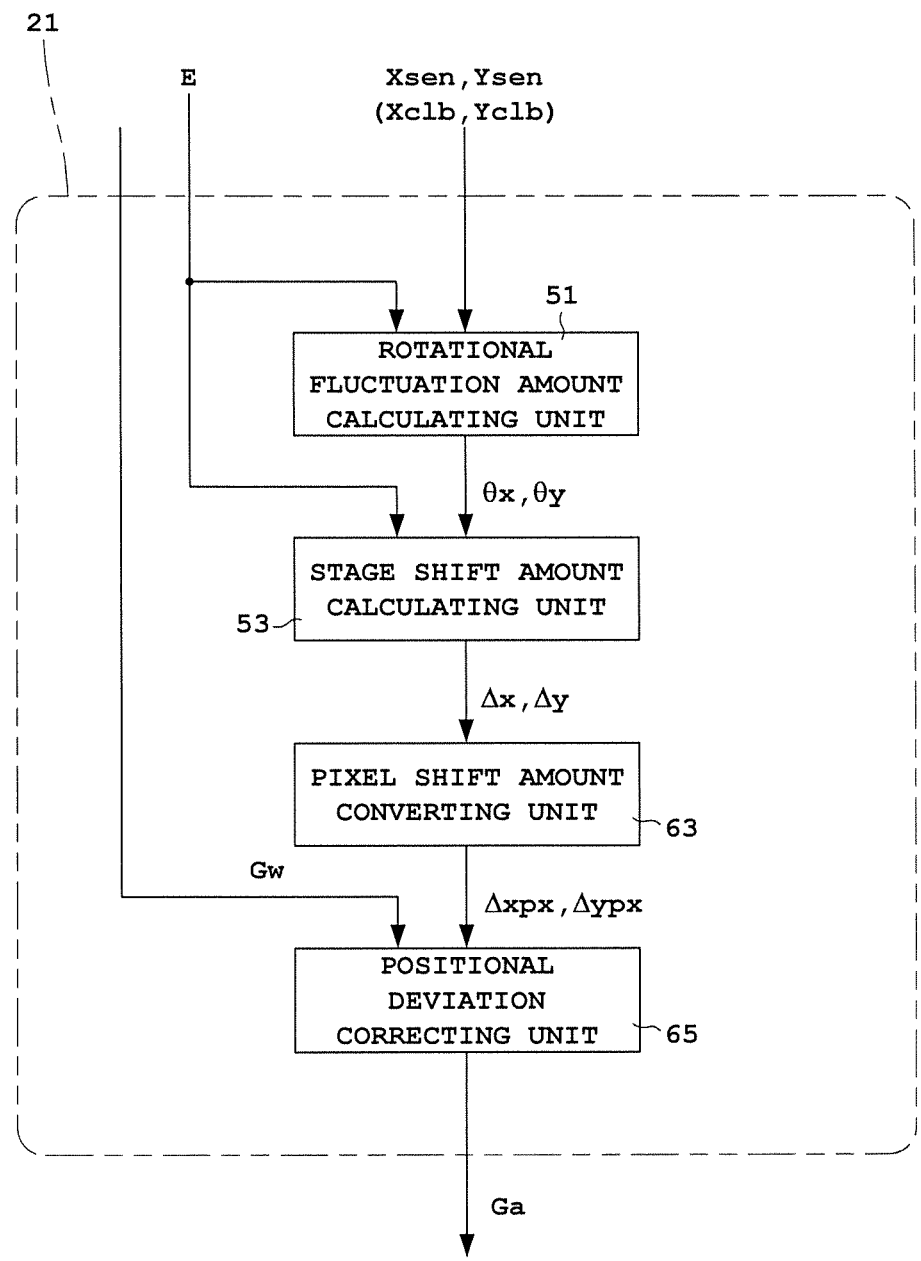
FIG. 12 illustrates a calculating unit according to another embodiment of the present invention.
Figure 13:
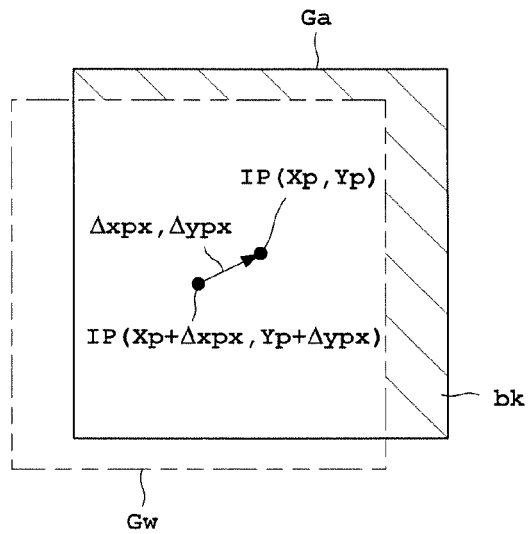
FIG. 13 is an explanatory view for illustrating operation of a positional deviation correcting unit according to the other embodiment.

The following describes another embodiment of the present invention with reference to drawings. The present embodiment is equal to Embodiment 1 in configuration until the stage shift amounts Δx and Δy are obtained. However, in the present embodiment, stage shift amounts Δx and Δy are converted into pixel shift amounts Δxpx and Δypx with pixels, and a projection image Gw is moved in a direction in which the converted pixel shift amounts Δxpx and Δypx are eliminated. Consequently, a tracking function of fluoroscopy that always tracks the attention point of the inspection object W at the center allows generation of a projection image Gw with high-accurate positioning even when the repeat positioning accuracy is insufficient. FIG. 12 illustrates a calculating unit according to Embodiment 2. FIG. 13 is an explanatory view of operation of a positional deviation correcting unit according to Embodiment 2. Here, the description in Embodiment 2 common to that of Embodiment 1 is to be omitted.

Reference is made to FIG. 12. In the present embodiment, the calculating unit 21 includes a pixel shift amount converting unit 63 and a positional deviation correcting unit 65, instead of the parameter changing unit 55, the image reconstructing unit 57, the parameter calculating unit 59, and the memory unit 61 in FIG. 7. The pixel shift amount converting unit 63 converts the stage shift amounts Δx and Δy into pixel shift amounts Δxpx and Δypx on the projection image Gw obtained by the FPD 4. The positional deviation correcting unit 65 moves the projection image Gw in a direction in which the positional deviation is eliminated for correction in accordance with the pixel shift amounts Δxpx and Δypx.

The positional deviation correcting unit 65 performs correction to obtain an imaging position IP(Xp,Yp) by removing the pixel shift amounts Δxpx and Δypx from the imaging position IP (Xp+Δxpx, Yp+Δypx) containing the pixel shift amounts Δxpx and Δypx, as illustrated in FIG. 13. Here, the numeral Ga denotes the corrected projection image. The numeral bk denotes an area with no data.

In the present embodiment, the stage shift amounts Δx and Δy are calculated in the same manner as Embodiment 1. The stage shift amounts Δx and Δy are positional deviations of the stage 2 in the X-axis and Y-axis directions at the imaging position IP caused by the attitude variation of the stage 2 in the yawing direction B, and thus correspond to errors in repeated positioning. The stage shift amounts Δx and Δy is converted into the pixel shift amounts Δxpx and Δypx on the projection image Gw. The projection image Gw is moved in a direction in which the positional deviation is eliminated in accordance with the converted pixel shift amounts Δxpx and Δypx. Consequently, a tracking function that always tracks the attention point of the inspection object W at the center allows generation of a projection image Gw with high-accurate positioning even when the repeat positioning accuracy is insufficient.

<Embodiment 3>

Figure 14:
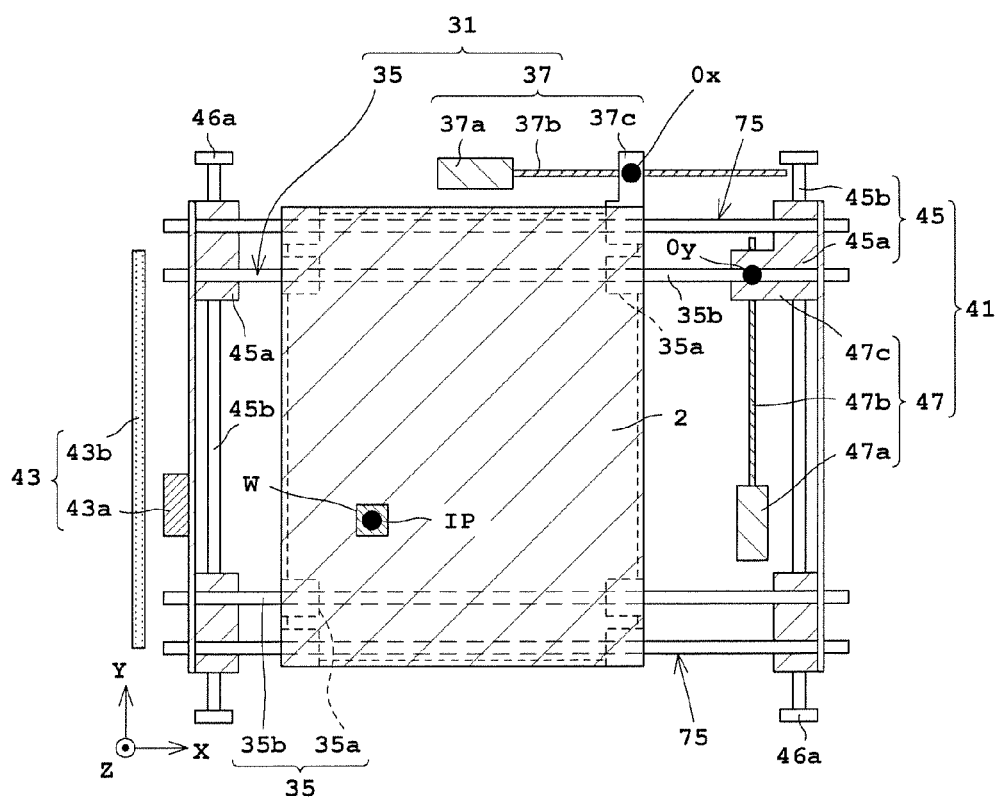
FIG. 14 is a plan view of a stage and its surroundings according to another embodiment of the present invention.

The following describes Embodiment 3 with reference to drawings. In Embodiments 1 and 2, the stage 2 is moved in the two directions along the X-axis and the Y-axis. The X-axis and Y-axis guiding units 35 and 45, the X-axis and Y-axis stage drive units 37 and 47, and the X-axis and Y-axis position detecting sensors 35 and 45 are disposed in the X-axis and Y-axis moving directions, respectively. In contrast to this, in Embodiment 3, a restraint force of the yawing direction B in one of the moving directions is enhanced, and position detecting sensors are disposed in the other of the moving directions. This allows calculation of the stage shift amounts Δx and Δy with an enhanced restraint force of the yawing direction B and a suppressed deviation of the stage 2. FIG. 14 is a plan view of the stage 2 and its surroundings in Embodiment 3. Here, the description of Embodiment 3 common to those of Embodiments 1 and 2 is to be omitted.

Reference is made to FIG. 14. The stage 2 is movable in the two directions along the X-axis, and the Y-axis, i.e., an X-direction and a Y-direction. X-axis and Y-axis guiding unit 35 and 45 and X-axis and Y-axis stage drive units 37 and 47 are disposed in the X-direction and Y-direction, respectively. Moreover, X-axis guiding units 75 are additionally disposed in one of the X-direction and Y-direction. For instance, the X-axis guiding units 75 are disposed in parallel in the Y-axis direction orthogonal to the X-axis moving direction. That is, two (a plurality of) types of X-axis guiding units 35 and 75 are disposed individually on both edges of the stage 2 in the Y-axis direction. Moreover, a Y-axis position detecting sensor 43 is disposed in the other of the X-direction and the Y-direction (e.g., the Y-axis direction in FIG. 14). Here, a plurality of Y-axis guiding units 45 may be disposed to provide an X-axis position detecting sensor 33.

In the present embodiment, no X-axis position detecting sensor 33 but the Y-axis position detecting sensor 43 is only provided. In such a case, equation transformation like transformation of the variable in the Equations (1) to (4) to a constant allows calculation of the stage shift amounts Δx and Δy in the same manner as Embodiments 1 and 2.

Moreover, the following is preferable for forming the X-axis and Y-axis stage moving mechanisms 31 and 41 in FIG. 14. That is, the X-axis and Y-axis position detecting sensors 33 and 43 are disposed on either the X-axis or the Y-axis in the moving direction in which a gap Dx or Dy between the X-axis and Y-axis guiding units 35 and 45 on one edge of the stage 2 and the X-axis and Y-axis stage drive units 37 and 47 of the stage 2 is longer.

That is, it is assumed as illustrated in FIG. 5A that the X-axis and Y-axis guiding units 35 and 45 have gaps Dx and Dy from the X-axis and Y-axis stage drive units 37 and 47, respectively, and a relationship of the distances of Dy>Dx exists. In this case, the Y-axis position detecting sensor 43 is disposed in the Y-axis direction with the gap Dy larger than the distance Dx, i.e., adjacent to the Y-axis stage moving mechanism 41.

In other words, an attitude variation of the stage 2 becomes large in either the X- or Y-direction in which the gap Dx or Dy between the X-axis and Y-axis guiding units 35 and 45 and the X-axis and Y-axis stage drive units 37 and 47, respectively, is larger. Accordingly, the attitude variation of the stage 2 is detectable in a wide range with the arrangement of the X-axis and Y-axis position detecting sensors 33 and 43. This allows high-accurate calculation of the stage shift amounts Δx and Δy.

In the present embodiment, the X-axis and Y-axis guiding units 35 and 45 are additionally disposed in one of the X-direction and the Y-direction. This achieves an enhanced restraint force of the stage 2 in the yawing direction B. Moreover, the X-axis and Y-axis position detecting sensors 33 and 43 are disposed on the other of the X-direction and the Y-direction. This also allows calculation of the stage shift amounts Δx and Δy from the positional information Xsen and Ysen detected by the X-axis and Y-axis position detecting sensors 33 and 43, respectively.

The present invention is not limited to the foregoing examples, but may be modified as follows.

(1) In the embodiments mentioned above, the rotational fluctuation amounts θx and θy are each calculated from the Equation (1) or (2). In contrast to this, the rotational fluctuation amounts θx and θy may be calculated from the following Equations (5). Specifically, the rotational fluctuation amounts θx and θy are extremely small that are generated at the X-axis and Y-axis sliding parts 0x and 0y for every radiography. Accordingly, the rotational fluctuation amounts θx and θy after the movement of the stage are calculated from the Equation (5) approximate to Equation (2).

$$\theta_y = \tan^{-1}\left(\frac{\Delta Y_{sen} - \Delta Y_{ipt}}{L_y}\right) \qquad (5)$$

$$\theta_x = \tan^{-1}\left(\frac{\Delta X_{sen} - \Delta X_{ipt}}{L_x}\right)$$

where, ΔXsen and AYsen are each a difference in sensor value between prior to and subsequent to the stage movement, ΔXipt and ΔYipt are each a difference in command value of the X-axis and Y-axis stage drive units 37 and 47 between prior to and subsequent to the stage movement, Ly is a distance between the Y-axis direction sensor axis 43*d* and the Y-axis direction drive axis 47*d*, and Lx is a distance between the X-axis direction sensor axis 33*d* and the X-axis direction drive axis 37*d*.

Figure 15:
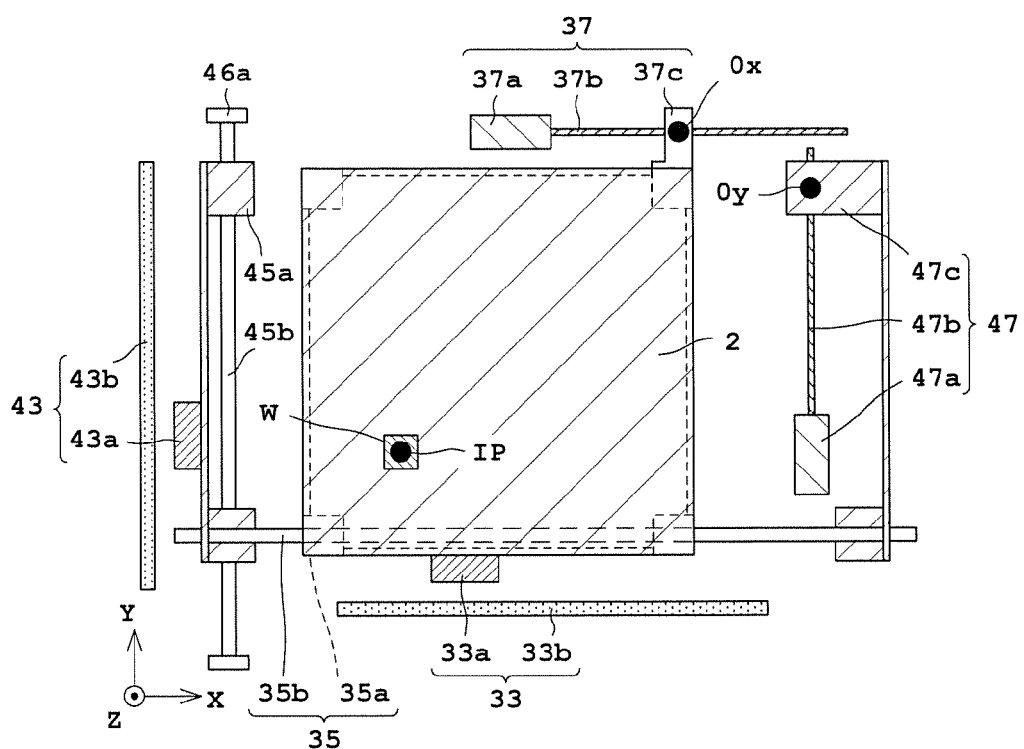
FIG. 15 is a plan view of a stage and its surroundings according to one modification of the present invention.

(2) In the embodiments and the modification (1) mentioned above, the X-axis and Y-axis guiding units 35 and 45 (, and 75) are disposed adjacent to both edges of the stage 2 as illustrated in FIGS. 5 and 14. In contrast to this, the X-axis and Y-axis stage drive units 37 and 47 may also serve as the X-axis and Y-axis guiding units 35 and 45 on one edge of both edges of the stage 2 adjacent to of the X-axis and Y-axis stage drive units 37 and 47. That is, as illustrated in FIG. 15, the X-axis and Y-axis guiding units 35 and 45 adjacent to the X-axis and Y-axis stage drive units 37 and 47 are removed, and the X-axis and Y-axis stage drive units 37 and 47 guide the stage 2 in the X-axis and Y-axis directions. This allows reduction in number of the X-axis and Y-axis guiding units 35 and 45, achieving an apparatus with lower costs and a compact configuration.

(3) In the embodiments and the modifications mentioned above, the stage 2 is moved in the two directions of the X-direction and the Y-direction in circular orbit around the rotation axis R on the X-Y plane orthogonal to the rotation axis R. In contrast to this, the stage 2 may be moved in one direction of the X-axis or Y-axis direction upon tomography. In this case, equation transformation is performed such as appropriate transformation of the variable in Equations (1) to (5) into a constant, allowing calculation of the stage shift amounts Δx and Δy in the same manner. When the stage 2 in FIG. 4 is moved only in the X-axis direction, the FPD 4 is tilted with the detector tilting drive unit 7 in synchronization with the movement of the stage 2.

(4) The embodiments and the modifications mentioned above each describe the X-ray inspecting apparatus 1. Alternatively, a γ-ray inspecting apparatus may be adopted that emits γ-rays from a source to the inspection object W and detects γ-rays passing through the inspection object W with γ-ray detectors to obtain the projection image Gw.

(5) In the embodiments and the modifications mentioned above, tomography or other types of inspection (e.g., fluoroscopy) is conducted by rotating the stage 2 and the FPD 4 around the rotation axis R. In contrast to this, the X-ray tube 3, instead of the FPD 4, may be rotated around the rotation axis R in synchronization with the movement of the stage 2. Alternatively, the stage 2, the X-ray tube 3, and the FPD 4 may be rotated around the rotation axis R. When the X-ray tube 3 is driven, the X-ray tube 3 is tilted by an X-ray tube tilting drive unit, not shown, and is rotated by an X-ray tube rotating mechanism, not shown, around the rotation axis R. Here, the detector tilting drive unit 7, the detector rotating mechanism 8, the X-ray tube tilting drive unit, and the X-ray tube rotating mechanism, not shown, correspond to the imaging system drive unit in the present invention.

That is, when only the stage 2 is moved, the detector sometimes has difficulty in tracking the same attention point in the inspection object W. That is because the FPD 4 has restriction in size of the detection area, and the attention point may be out of the detection area of the FPD. Not only the stage 2 but also the X-ray tube 3 or the FPD 4 is driven, whereby the attention point in the inspection object W can be continuously tracked without falling out of the detection area of the FPD 4. This is useful when the attention point is required to be observed from various directions upon tomography or other inspection. Accordingly, even when the stage 2 is moved largely, the embodiments of the present invention allow suppression of the positional deviation at the same imaging position and in the same imaging direction.

(6) In the embodiments and modifications mentioned above, the stage 2 is moved in the two directions of the X-direction and the Y-direction. Alternatively, the stage may be moved in three or more directions.

The present invention may be embodied in other specific forms without departing from the spirit or essential attributes thereof and, accordingly, reference should be made to the appended claims, rather than to the foregoing specification, as indicating the scope of the invention.

The invention claimed is:

1. A radiation inspecting apparatus having a radiation source emitting X-ray radiation to an inspection object, a radiation detector detecting X-ray radiation passing through the inspection object to capture projection images, and a stage disposed between the radiation source and the radiation detector for supporting the inspection object placed thereon, the stage being held movably in a substantially linear direction relative to guiding units, the radiation inspecting apparatus comprising:

a stage drive unit transmitting driving power to the stage for moving the stage;

a position detecting sensor detecting a position of the stage;

a rotational fluctuation amount calculating unit calculating a rotational fluctuation amount of the stage representing inclination of the stage relative to the guiding units in accordance with detected positional information from the position detecting sensor upon imaging of the inspection object;

a stage shift amount calculating unit calculating a stage shift amount in accordance with the rotational fluctuation amount; and an image reconstructing unit correcting a positional deviation of the stage in accordance with the stage shift amount and reconstructing the images.

2. The radiation inspecting apparatus according to claim 1, wherein the rotational fluctuation amount calculating unit calculates the rotational fluctuation amount of the stage in accordance with the detected positional information from the position detecting sensor upon calibration of the stage drive unit with a calibration phantom and the detected positional information from the position detecting sensor upon the imaging of the inspection image.

3. The radiation inspecting apparatus according to claim 1, wherein the stage drive unit is disposed adjacent to a first edge of the stage, and the position detecting sensor is disposed adjacent to a second edge of the stage opposite to the first edge.

4. The radiation inspecting apparatus according to claim 2, wherein the stage drive unit is disposed adjacent to a first edge of the stage, and the position detecting sensor is disposed adjacent to a second edge of the stage opposite to the first edge.

5. The radiation inspecting apparatus according to claim 1, wherein the stage is moved in at least two directions along an X-axis and a Y-axis, the stage drive unit is provided along each of the X-axis and the Y-axis, and guiding units are each disposed in parallel on both edges of the stage in a direction orthogonal to a moving direction thereof, the guiding units guiding the stage in the moving direction, and an additional guiding unit is disposed on only one of the X-axis and the Y-axis in the direction orthogonal to the moving direction, and the position detecting sensor is provided on the other of the X-axis and the Y-axis.

6. The radiation inspecting apparatus according to claim 2, wherein
the stage is moved in at least two directions along an X-axis and a Y-axis,
the stage drive unit is provided along each of the X-axis and the Y-axis, and guiding units are each disposed in parallel on both edges of the stage in a direction orthogonal to a moving direction thereof, the guiding units guiding the stage in the moving direction, and
an additional guiding unit is disposed on only one of the X-axis and the Y-axis in the direction orthogonal to the moving direction, and the position detecting sensor is provided on the other of the X-axis and the Y-axis.

7. The radiation inspecting apparatus according to claim 3, wherein
the stage is moved in at least two directions along an X-axis and a Y-axis,
the stage drive unit is provided along each of the X-axis and the Y-axis, and guiding units are each disposed in parallel on both edges of the stage in a direction orthogonal to a moving direction thereof, the guiding units guiding the stage in the moving direction, and
an additional guiding unit is disposed on only one of the X-axis and the Y-axis in the direction orthogonal to the moving direction, and the position detecting sensor is provided on the other of the X-axis and the Y-axis.

8. The radiation inspecting apparatus according to claim 5, wherein
the position detecting sensor is disposed on either the X-axis or the Y-axis with a larger gap, the larger gap being recognized through comparison of a gap between the guiding unit on one of the edges of the stage along the X-axis disposed opposite to the stage drive unit on the X-axis and the stage drive unit on the X-axis with a gap between the guiding unit on one of the edges of the stage along the Y-axis disposed opposite to the stage drive unit on the Y-axis and the stage drive unit on the Y-axis.

9. The radiation inspecting apparatus according to claim 1, wherein
the stage is moved in at least two moving directions along the X-axis and the Y-axis, and
the stage drive unit and the position detecting sensor are provided in each of the moving directions.

10. The radiation inspecting apparatus according to claim 2, wherein
the stage is moved in at least two moving directions along the X-axis and the Y-axis, and
the stage drive unit and the position detecting sensor are provided in each of the moving directions.

11. The radiation inspecting apparatus according to claim 3, wherein
the stage is moved in at least two moving directions along the X-axis and the Y-axis, and
the stage drive unit and the position detecting sensor are provided in each of the moving directions.

12. The radiation inspecting apparatus according to claim 1, further comprising:
an imaging system drive unit driving at least either the radiation source or the radiation detector.

13. A radiation inspecting apparatus having a radiation source emitting X-ray radiation to an inspection object, a radiation detector detecting X-ray radiation passing through the inspection object to capture a projection image, and a stage disposed between the radiation source and the radiation detector for supporting the inspection object placed thereon, the stage being held movably in a substantially linear direction relative to guiding units, the radiation inspecting apparatus comprising:
a stage drive unit transmitting driving power to the stage for moving the stage;
a position detecting sensor detecting a position of the stage;
a rotational fluctuation amount calculating unit calculating a rotational fluctuation amount of the stage representing inclination of the stage relative to the guiding units in accordance with detected positional information from the position detecting sensor upon imaging of the inspection object;
a stage shift amount calculating unit calculating a stage shift amount in accordance with the rotational fluctuation amount;
a pixel shift amount converting unit converting the stage shift amount into a pixel shift amount on the projection image; and
a positional deviation correcting unit moving the projection image in accordance with the pixel shift amount in a direction in which a positional deviation is eliminated.

* * * * *